(12) United States Patent
Goodwin et al.

(10) Patent No.: US 11,725,171 B2
(45) Date of Patent: Aug. 15, 2023

(54) FLUID MIXING SYSTEMS WITH ADJUSTABLE MIXING ELEMENT

(71) Applicant: LIFE TECHNOLOGIES CORPORATION, Carlsbad, CA (US)

(72) Inventors: Michael E. Goodwin, Logan, UT (US); Nephi D. Jones, Newton, UT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 991 days.

(21) Appl. No.: 16/502,245

(22) Filed: Jul. 3, 2019

(65) Prior Publication Data

US 2019/0322971 A1 Oct. 24, 2019

Related U.S. Application Data

(62) Division of application No. 13/659,616, filed on Oct. 24, 2012, now Pat. No. 10,435,658.

(Continued)

(51) Int. Cl.
*C12M 1/00* (2006.01)
*C12M 3/00* (2006.01)
(Continued)

(52) U.S. Cl.
CPC ........... *C12M 23/14* (2013.01); *B01F 27/071* (2022.01); *B01F 27/113* (2022.01);
(Continued)

(58) Field of Classification Search
CPC ....... C12M 23/16; C12M 23/26; C12M 23/14
See application file for complete search history.

(56) References Cited

U.S. PATENT DOCUMENTS 5,356,214 A 10/1994 Styles
5,728,581 A * 3/1998 Schwartz ............... C12M 23/02
435/372

(Continued)

FOREIGN PATENT DOCUMENTS

DE 202010005709 9/2010
DE 10 2009 041569 4/2011
(Continued)

OTHER PUBLICATIONS

International Search Report and Written Opinion dated Feb. 4, 2013 issued in PCT Application No. PCT/US2012/061708.
(Continued)

*Primary Examiner* — Jonathan M Hurst
(74) *Attorney, Agent, or Firm* — Mintz, Levin, Cohn, Ferris, Glovsky and Popeo, P.C.

(57) ABSTRACT

A fluid mixing system includes a support housing having an interior surface bounding a chamber. A flexible bag is disposed within the chamber of the support housing, the flexible bag having an interior surface bounding a compartment. An impeller is disposed within the chamber of the flexible bag. A drive shaft is coupled with the impeller such that rotation of the drive shaft facilitates rotation of the impeller. A drive motor assembly is coupled with the draft shaft and is adapted to rotate the drive shaft. An adjustable arm assembly is coupled with the drive motor assembly and is adapted to move the drive motor assembly which in turn moves the position of the drive shaft and impeller. An electrical controller can control movement of the adjustable arm.

12 Claims, 18 Drawing Sheets

Related U.S. Application Data

(60) Provisional application No. 61/551,159, filed on Oct. 25, 2011.

(51) Int. Cl.

| | | |
|---|---|---|
| *C12M 1/06* | (2006.01) | |
| *C12M 1/34* | (2006.01) | |
| *B01F 27/61* | (2022.01) | |
| *B01F 27/07* | (2022.01) | |
| *B01F 27/113* | (2022.01) | |
| *B01F 27/213* | (2022.01) | |
| *B01F 27/2121* | (2022.01) | |
| *B01F 27/231* | (2022.01) | |
| *B01F 33/00* | (2022.01) | |
| *B01F 35/513* | (2022.01) | |
| *B01F 35/22* | (2022.01) | |
| *B01F 35/71* | (2022.01) | |

(52) U.S. Cl.
CPC ........ *B01F 27/213* (2022.01); *B01F 27/2121* (2022.01); *B01F 27/2312* (2022.01); *B01F 27/61* (2022.01); *B01F 33/86* (2022.01); *B01F 35/2209* (2022.01); *B01F 35/513* (2022.01); *C12M 23/26* (2013.01); *C12M 23/48* (2013.01); *C12M 23/52* (2013.01); *C12M 27/02* (2013.01); *C12M 27/06* (2013.01); *C12M 41/00* (2013.01); *B01F 35/715* (2022.01)

(56) References Cited

U.S. PATENT DOCUMENTS

| | | | |
|---|---|---|---|
| 6,083,587 A | 7/2000 | Smith et al. | |
| 6,617,146 B1 | 9/2003 | Naccarato et al. | |
| 6,908,223 B2 | 6/2005 | Bibbo et al. | |
| 7,086,778 B2 | 8/2006 | Terentiev | |
| 7,384,027 B2 | 6/2008 | Terentiev | |
| 7,384,783 B2 | 6/2008 | Kunas | |
| 7,434,983 B2 | 10/2008 | Terentiev | |
| 7,469,884 B2 | 12/2008 | Terentiev | |
| 7,481,572 B2 | 1/2009 | Terentiev | |
| 7,682,067 B2 | 3/2010 | West et al. | |
| 7,695,186 B2 | 4/2010 | Terentiev | |
| 7,879,599 B2 | 2/2011 | Goodwin et al. | |
| 2002/0131654 A1 | 9/2002 | Smith et al. | |
| 2003/0077466 A1 | 4/2003 | Smith et al. | |
| 2005/0130291 A1* | 6/2005 | Erhardt ................. | C12M 23/08 422/209 |
| 2006/0196501 A1 | 9/2006 | Bibbo | |
| 2006/0240546 A1* | 10/2006 | Goodwin ............... | C12M 23/14 435/289.1 |
| 2006/0270036 A1 | 11/2006 | Goodwin et al. | |
| 2006/0280028 A1 | 12/2006 | West et al. | |
| 2008/0068920 A1* | 3/2008 | Galliher ................. | B29C 45/16 239/66 |
| 2008/0186802 A1 | 8/2008 | Bungay | |
| 2009/0116335 A1* | 5/2009 | Wild .................... | B01F 35/4111 366/249 |
| 2010/0015696 A1 | 1/2010 | Claes | |
| 2010/0097882 A1 | 4/2010 | Uhlenkamp | |
| 2010/0149908 A1 | 6/2010 | Singh et al. | |
| 2010/0159524 A1 | 6/2010 | Smith et al. | |
| 2011/0188928 A1 | 8/2011 | West et al. | |
| 2011/0310696 A1 | 12/2011 | Goodwin et al. | |
| 2012/0113741 A1 | 5/2012 | Filipitsch | |

FOREIGN PATENT DOCUMENTS

| | | |
|---|---|---|
| EP | 1 321 756 A2 | 6/2003 |
| EP | 1 762 607 A1 | 3/2007 |
| JP | 2001/92117 A | 5/2011 |
| JP | 2011-092117 A | 5/2011 |

OTHER PUBLICATIONS

Bioreactor System, publicly disclosed by HyClone Laboratories, Inc., at least as early as Oct. 24, 2010, 6 pages.

Measures of Turbidity in Water (Ohio State), Jul. 1, 2004.

*Evaluating Disposable Mixing Systems*, BioPharm (Feb. 1, 2009) (Year: 2009).

European Examination Report dated Jun. 4, 2018, issued in EP Application No. 12787244.

\* cited by examiner

FLUID MIXING SYSTEMS WITH ADJUSTABLE MIXING ELEMENT

CROSS-REFERENCE TO RELATED APPLICATIONS

This application is a Division of U.S. application Ser. No. 13/659,616 filed Oct. 24, 2012, now U.S. Pat. No. 10,435,658, issued Oct. 8, 2019, which claims priority to U.S. application No. 61/551,159 filed Oct. 25, 2011, which disclosures are herein incorporated by reference in their entirety.

BACKGROUND OF THE INVENTION

1. The Field of the Invention

The present invention relates to methods and systems for mixing fluids, namely, biological fluids.

2. The Relevant Technology

The biopharmaceutical industry uses a broad range of mixing systems for a variety of processes such as in the preparation of media and buffers and in the growing of cells and microorganisms in bioreactors. Some conventional mixing systems, including bioreactors, comprise a flexible bag disposed within a rigid support housing. An impeller is disposed within the flexible bag and is used to mix or suspend the solution within the bag. In some embodiments, the impeller is mounted to the bottom of the bag and is magnetically driven. In other embodiments, the impeller is fixed on the end of a drive shaft that projects into the flexible bag. In both embodiments, however, the impeller is designed to remain at a substantially fixed position which is optimal for mixing a narrowly defined volume of solution in the flexible bag. To enable homogeneous mixing of larger volumes of solution, larger bags are used that have an impeller positioned at a location that is optimal for that size of bag.

In some processing procedures it can be desirable to initially mix solutions at a low volume and then progressively increase the volume of the solution. For example, this is a common procedure used with bioreactors for growing cells. The process typically entails dispensing a seed inoculum in a growth media contained within a relatively small bag and then transferring the solution to progressively larger bags where additional media is added as the cells grow and multiple. This process is repeated until a final desired volume is achieved. By transferring the solution to different sized bags which each have a corresponding mixer, the operator can ensure homogeneous mixing of each of the different volumes.

Although the above process of moving solutions to different sized bags to maintain proper mixing and suspension is functional, the procedure has some shortcomings. For example, the necessity of stepping to different sized bags is labor intensive, time consuming, and has high material costs in that the multiple bags are discarded after use. Furthermore, transferring between different bags produces some mixing down-time which can influence cell growth. In addition, the necessity of shifting between bags increases the risk of contamination to the solution and potential damage to the cells.

Accordingly, what is needed in the art are improved mixing systems that solve all or some of the above problems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

The present invention relates to systems and methods for mixing and, if desired, sparging solutions and/or suspensions. The systems can be commonly used as bioreactors or fermentors for culturing cells or microorganisms. By way of example and not by limitation, the inventive systems can be used in culturing bacteria, fungi, algae, plant cells, animal cells, protozoan, nematodes, and the like. The systems can accommodate cells and microorganisms that are aerobic or anaerobic and are adherent or non-adherent. The systems can also be used in association with the formation and/or treatment of solutions and/or suspensions that are for biological purposes, such as media, buffers, or reagents. The systems can also be used for mixing powders or other components into a liquid where sparging is not required and/or where is solution is not for biological purposes.

Some embodiments of the inventive systems are designed so that a majority of the system components that contact the material being processed can be disposed of after each use. As a result, the inventive systems substantially eliminate the burden of cleaning and sterilization required by conventional stainless steel mixing systems. This feature also ensures that sterility can be consistently maintained during repeated processing of multiple batches. The inventive systems are also adjustable so that they can be used for mixing a variety of different batch sizes. In view of the foregoing, and the fact that the inventive systems are easily scalable, relatively low cost, and easily operated, the inventive systems can be used in a variety of industrial and research facilities that previously outsourced such processing.

Some embodiments of the present invention also enable manual or automatic adjustment of the position, tilt, and/or movement pattern of the mixing element within the solution. This ability to adjust the position, tilt, and/or movement pattern of the mixing element enables optimal mixing or suspension of the solution as the volume, properties or critical processing parameters of the solution varies.

Figure 1:
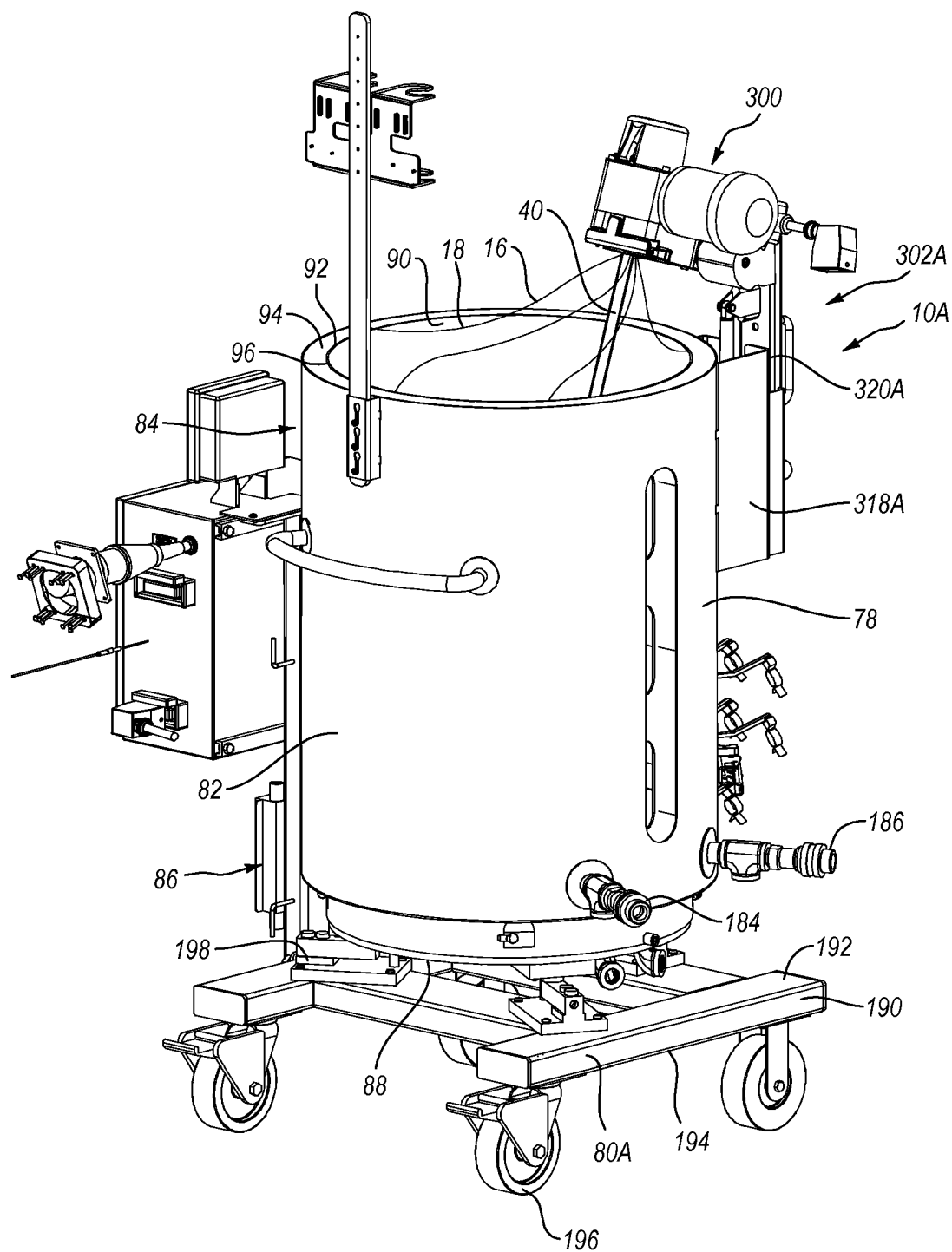
FIG. 1 is a perspective view of a fluid mixing system.

Depicted in FIG. 1 is one embodiment of an inventive mixing system 10A incorporating features of the present invention. In general, mixing system 10A comprises a support housing 78, a cart 80A on which on which support housing 78 rests, a drive motor assembly 300, an adjustable arm assembly 302A which supports drive motor assembly 300 on support housing 78, a container assembly 16 that is supported within support housing 78, and drive shaft 362 (FIG. 3) that extends between drive motor assembly 300 and container assembly 16. The various components of mixing system 10A will now be discussed in greater detail.

Figure 2:
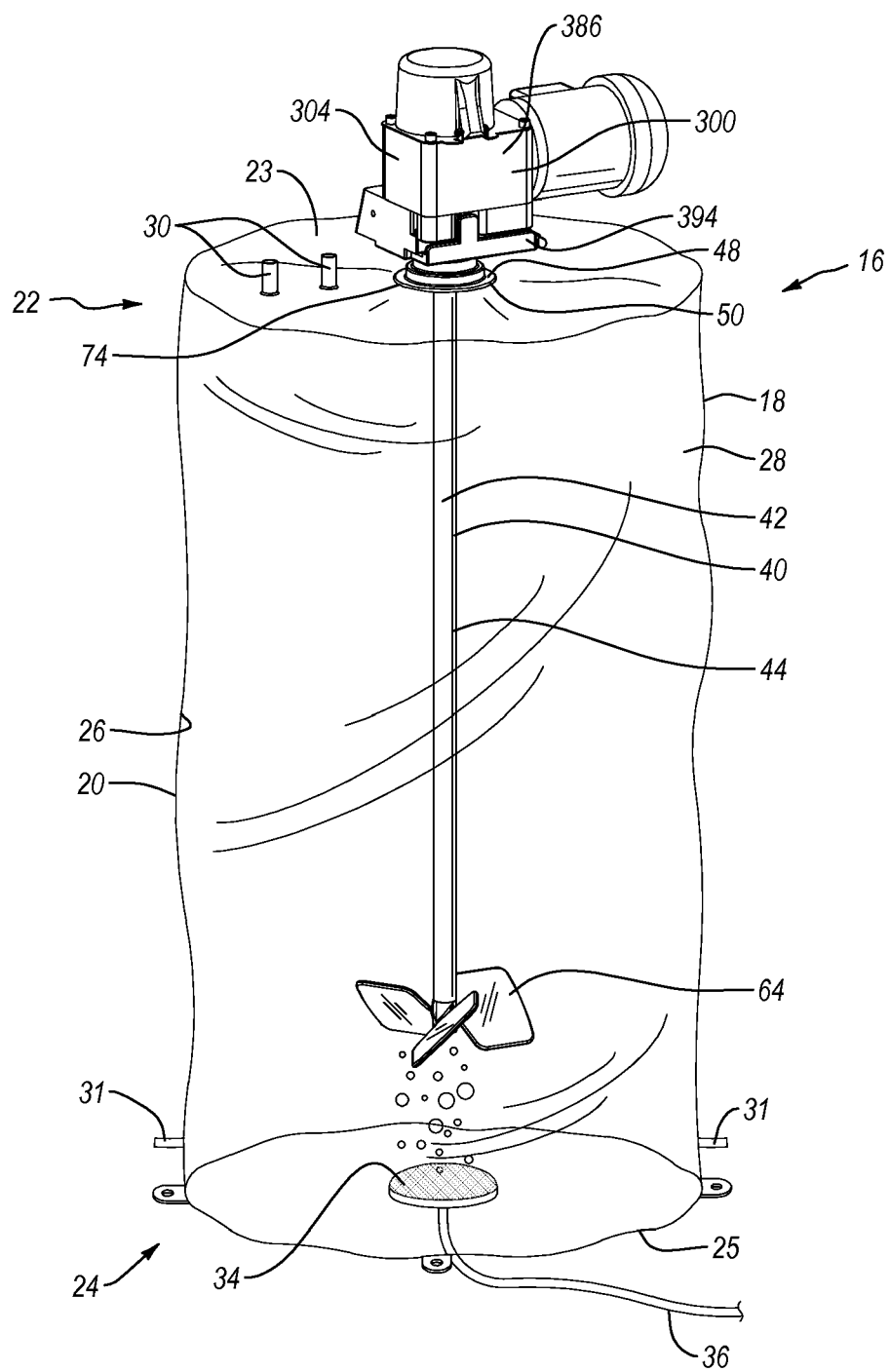
FIG. 2 is a perspective view of the container assembly of the fluid mixing system shown in FIG. 1.

As depicted in FIG. 2, container assembly 16 comprises a container 18 having a side 20 that extends from an upper end 22 to an opposing lower end 24. Upper end 22 terminates at an upper end wall 23 while lower end 24 terminates at a lower end wall 24. Container 18 also has an interior surface 26 that bounds a compartment 28. Compartment 28 is configured to hold a fluid. In the embodiment depicted, container 18 comprises a flexible bag that is comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083, 587 which issued on Jul. 4, 2000, United States Patent Publication No. US 2003/0077466 A1, published Apr. 24, 2003, and United States Patent Publication No. US 2011/0310696 A1, published Dec. 22, 2011 which are incorporated herein by specific reference.

In one embodiment, container 18 comprise a two-dimensional pillow style bag such as where two sheets of material are placed in overlapping relation and the two sheets are bonded together at their peripheries to form the internal compartment. In other embodiments, as depicted in FIG. 2, container 18 can comprise a three-dimensional bag that not only has an annular side wall but also a two dimensional top end wall and a two dimensional bottom end wall. Further disclosure with regard to three-dimensional bags and method of manufacturing are disclosed in United States Patent Publication No. US 2002-0131654 A1, published Sep. 19, 2002 and United States Patent Publication No. US 2011/0310696 A1, published Dec. 22, 2011 which are incorporated herein by specific reference.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 18 can be any shape, in one embodiment container 18 is specifically configured to be complementary or substantially complementary to the chamber of support housing 78 in which container 18 is received so that container 18 is properly supported therein when filled with fluid.

Although in the above discussed embodiment container 18 has a flexible, bag-like configuration, in alternative embodiments it is appreciated that container 18 can comprise any form of collapsible container or semi-rigid container. For example, the container can be accordioned or contain baffles that permit the container to expand and contract. In other embodiments, portions of the container can be rigid while other portions are flexible. Container 18 can also be transparent or opaque and can have ultraviolet light inhibitors incorporated therein.

Continuing with FIG. 2, formed on container 18 are a plurality of ports 30 at upper end 22 and a plurality of ports 31 at lower end 24. Each of ports 30, 31 communicate with compartment 28. Although only a few ports 30, 31 are shown, it is appreciated that container 18 can be formed with any desired number of ports 30, 31 and that ports 30, 31 can be formed at any desired location on container 18 including along side 20 and on upper end wall 23 an lower end wall 25. Ports 30, 31 can be the same configuration or different configurations and can be used for a variety of different purposes. For example, ports 30, 31 can be coupled with fluid lines for delivering media, cell cultures, gases and/or other components into container 18 and also withdrawing gases and fluids from container 18.

Ports 30, 31 can also be used for coupling probes and/or sensors to container 18. For example, when container 18 is used as a bioreactor for growing cells or microorganisms, ports 30, 31 can be used for coupling probes such as temperatures probes, pH probes, dissolved oxygen probes, dissolved $CO_2$ probes and the like. Various optical sensors and other types of sensors can also be attached to ports 30, 31. Examples of ports 30, 31 and how various probes, sensors, and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 30, 31 can also be used for coupling container 18 to secondary containers, to condenser systems, and to other desired fittings.

In one embodiment of the present invention, container assembly 16 includes means for delivering a gas into the lower end of container 18. By way of example and not by limitation, container assembly 16 can comprise a sparger 34 positioned either on or mounted to lower end 24 of container 18 for delivering a gas to the fluid within container 18. As is understood by those skilled in the art, various gases are typically required in the growth of cells or microorganisms within container 18. The gas typically comprises air that is selectively combined with oxygen, carbon dioxide and/or nitrogen. However, other gases can also be used. The addition of these gases can be used to regulate the dissolved oxygen content and pH of a culture. A gas line 36 is coupled with sparger 34 for delivering the desired gas to sparger 34. Gas line 36 need not pass through lower end 24 of container 18 but can extend down from upper end 22 or from other locations.

Sparger 34 can have a variety of different configurations. For example, sparger 34 can comprise a permeable membrane or a fritted structure comprised of metal, plastic or other materials that dispense the gas in small bubbles into container 18. Smaller bubbles can permit better absorption of the gas into the fluid. In other embodiments, sparger 34 can simply comprise a tube, port, or other type opening formed on or coupled with container 18 through which gas is passed into container 18. In contrast to being disposed on container 18, the sparger can also be formed on or coupled with impeller 64, which is discussed below. Examples of spargers and how they can be used in the present invention are disclosed in United States Patent Publication Nos. 2006/0270036 and 2006/0240546 which were previously incorporated by reference. Other conventional spargers can also be used.

Figure 3:
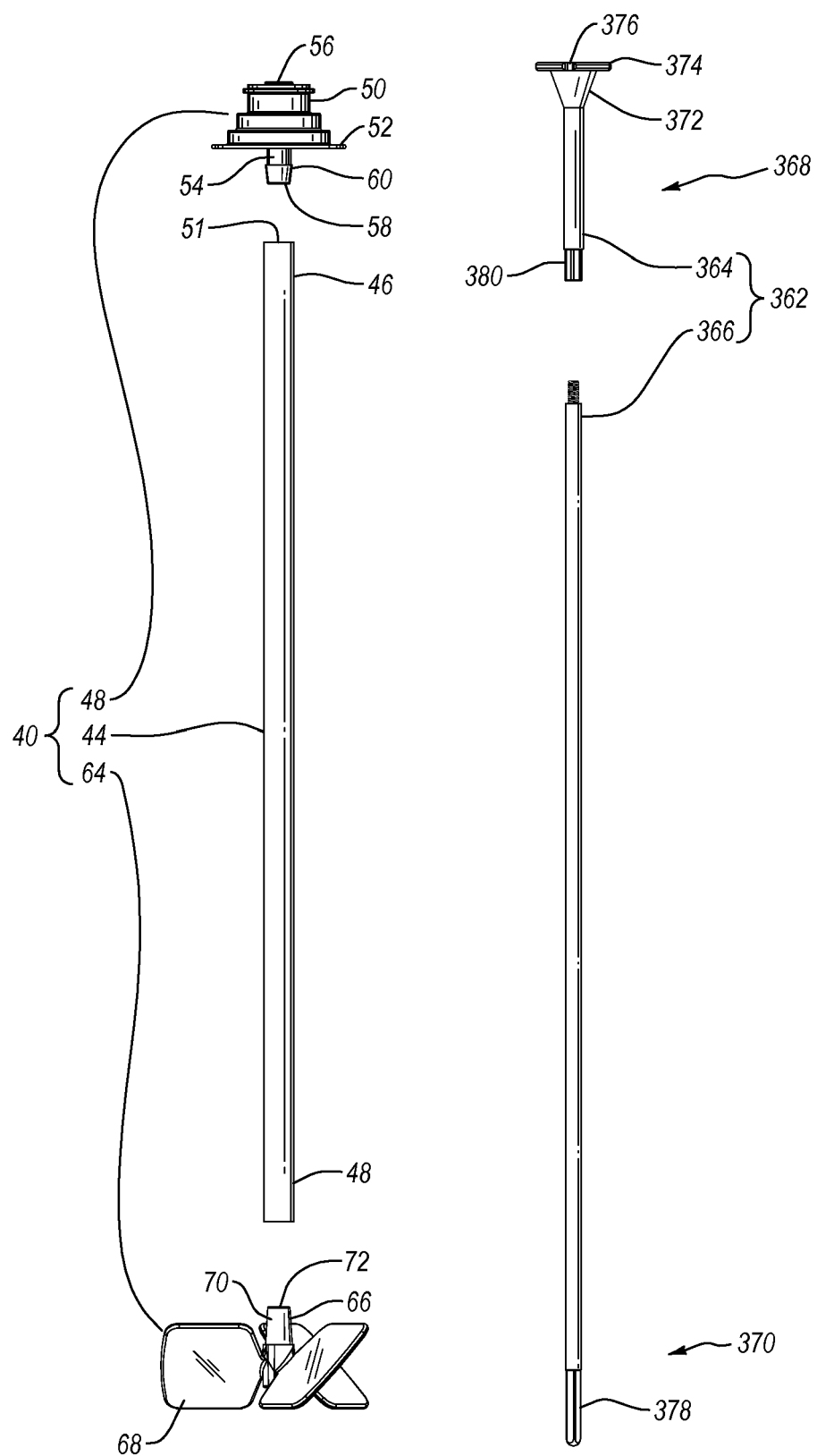
FIG. 3 is an elevated side view of an impeller assembly of the container assembly shown in FIG. 2 and a drive shaft.

Container assembly 16 further comprises an impeller assembly 40. As depicted in FIG. 3, impeller assembly 40 comprises an elongated tubular connector 44 having a rotational assembly 48 mounted at one end and an impeller 64 mounted on the opposing end. More specifically, tubular connector 44 has a first end 46 and an opposing second end 48 with a passage 51 that extends therebetween. In one embodiment, tubular connector 44 comprises a flexible tube such as a polymeric tube. In other embodiments, tubular connector 44 can comprise a rigid tube or other tubular structure.

Rotational assembly 48 is mounted to first end 46 of tubular connector 44. Rotational assembly 48 comprises an outer casing 50 having an outwardly projecting flange 52 and a tubular hub 54 rotatably disposed within outer casing 50. A bearing assembly can be disposed between outer casing 50 and tubular hub 54 to permit free and easy rotation of hub 54 relative to casing 50. Likewise, one or more seals can be formed between outer casing 50 and tubular hub 54 so that during use an aseptic seal can be maintained between outer casing 50 and tubular hub 54 as tubular hub 54 rotates relative to outer casing 50.

Hub 54 has an interior surface 56 that bounds an opening 58 extending therethrough. As will be discussed below in greater detail, an engaging portion of interior surface 56 has a polygonal or other non-circular transverse cross section so that a driver portion of drive shaft 362 passing through opening 58 can engage the engaging portion and facilitate rotation of hub 54 by rotation of drive shaft 362. Hub 54 can also comprise a tubular stem 60 projecting away from outer casing 50. Hub 54 can couple with first end 46 of tubular connector 44 by stem 60 being received within first end 46. A pull tie, clamp, crimp or other fastener can then be used to further secure stem 60 to tubular connect 44 so that a liquid tight seal is formed therebetween. Other conventional connecting techniques can also be used.

Impeller 64 comprises a central hub 66 having a plurality of fins 68 radially outwardly projecting therefrom. It is appreciated that a variety of different numbers and configurations of fins 68 can be mounted on hub 66. Hub 66 has a first end 70 with a blind socket 72 formed thereat. Socket 72 typically has a noncircular transverse cross section, such as polygonal, so that it can engage a driver portion of drive shaft 362. Accordingly, as will be discussed below in greater detail, when a driver portion is received within socket 72, the driver portion engages with impeller 64 such that rotation of drive shaft 362 facilities rotation of impeller 64.

In one embodiment, hub 66 and fins 68 of impeller 64 are molded from a polymeric material. In alternative embodiments, hub 66 and fins 68 can be made of metal, composite, or a variety of other materials. If desired, an annular insert can be positioned within socket 72 to help reinforce hub 66. For example, the insert can be comprised of metal or other material having a strength property greater than the material from which hub 66 is comprised.

Impeller 64 can be attached to connector 44 by inserting first end 70 of hub 66 within connector 44 at second end 48. A pull tie, clamp, crimp, or other type of fastener can then be cinched around second end 48 of connector 44 so as to form a liquid tight sealed engagement between impeller 64 and connector 44.

Returning to FIG. 2, rotational assembly 48 is secured to container 18 so that tubular connector 44 and impeller 64 extend into or are disposed within compartment 28 of container 18. Specifically, in the depicted embodiment container 18 has an opening 74 at upper end 22. Flange 52 of outer casing 50 is sealed around the perimeter edge bounding opening 74 so that hub 54 is aligned with opening 74. Tubular connector 44 having impeller 64 mounted on the end thereof projects from hub 54 (FIG. 3) into compartment 28 of container 18. In this configuration, outer casing 50 is fixed to container 18 but hub 54, and thus also tubular connector 44 and impeller 64, can freely rotate relative to outer casing 50 and container 18. As a result of rotational assembly 48 sealing opening 74, compartment 28 is sealed closed so that it can be used in processing sterile fluids.

As depicted in FIG. 3, impeller assembly 40 is used in conjunction with drive shaft 362. In general drive shaft 362 comprises a head section 364 and a shaft section 366 that can be coupled together by threaded connection or other techniques. Alternatively, drive shaft 362 can be formed as a single piece member or from a plurality of attachable sections. Drive shaft 362 has a first end 368 and an opposing second end 370. Formed at first end 368 is a frustoconical engaging portion 372 that terminates at a circular plate 374. Notches 376 are formed on the perimeter edge of circular plate 374 and are used for engaging drive shaft 362 with a drive motor assembly as will be discussed below.

Formed at second end 370 of drive shaft 362 is a driver portion 378. Driver portion 378 has a non-circular transverse cross section so that it can facilitate locking engagement within hub 66 of impeller 64. In the embodiment depicted, driver portion 378 has a polygonal transverse cross section. However, other non-circular shapes can also be used. A driver portion 380 is also formed along drive shaft 362 toward first end 368. Driver portion 380 also has a non-circular transverse cross section and is positioned so that it can facilitate locking engagement within the interior surface of hub 54 of rotational assembly 48.

During use, as will be discussed below in further detail, drive shaft 362 is advanced down through hub 54 of rotational assembly 48, through tubular connecter 44 and into hub 66 of impeller 64. As a result of the interlocking engagement of driver portions 378 and 380 with hubs 66 and 54, respectively, rotation of drive shaft 362 by a drive motor assembly facilitates rotation of hub 54, tubular connecter 44 and impeller 64 relative to outer casing 50 of rotational assembly 48. As a result of the rotation of impeller 64, fluid within container 18 is mixed.

It is appreciated that impeller assembly 40, drive shaft 362 and the discrete components thereof can have a variety of different configuration and can be made of a variety of different materials. Alternative embodiments of and further disclosure with respect to impeller assembly 40, drive shaft 362, and the components thereof are disclosed in US Patent Publication No. US 2011/0188928 A1, published Aug. 4, 2011 and US Patent Publication No. US 2011/0310696 A1, published Dec. 22, 2011 which are hereby incorporated by specific reference.

Figure 2A:
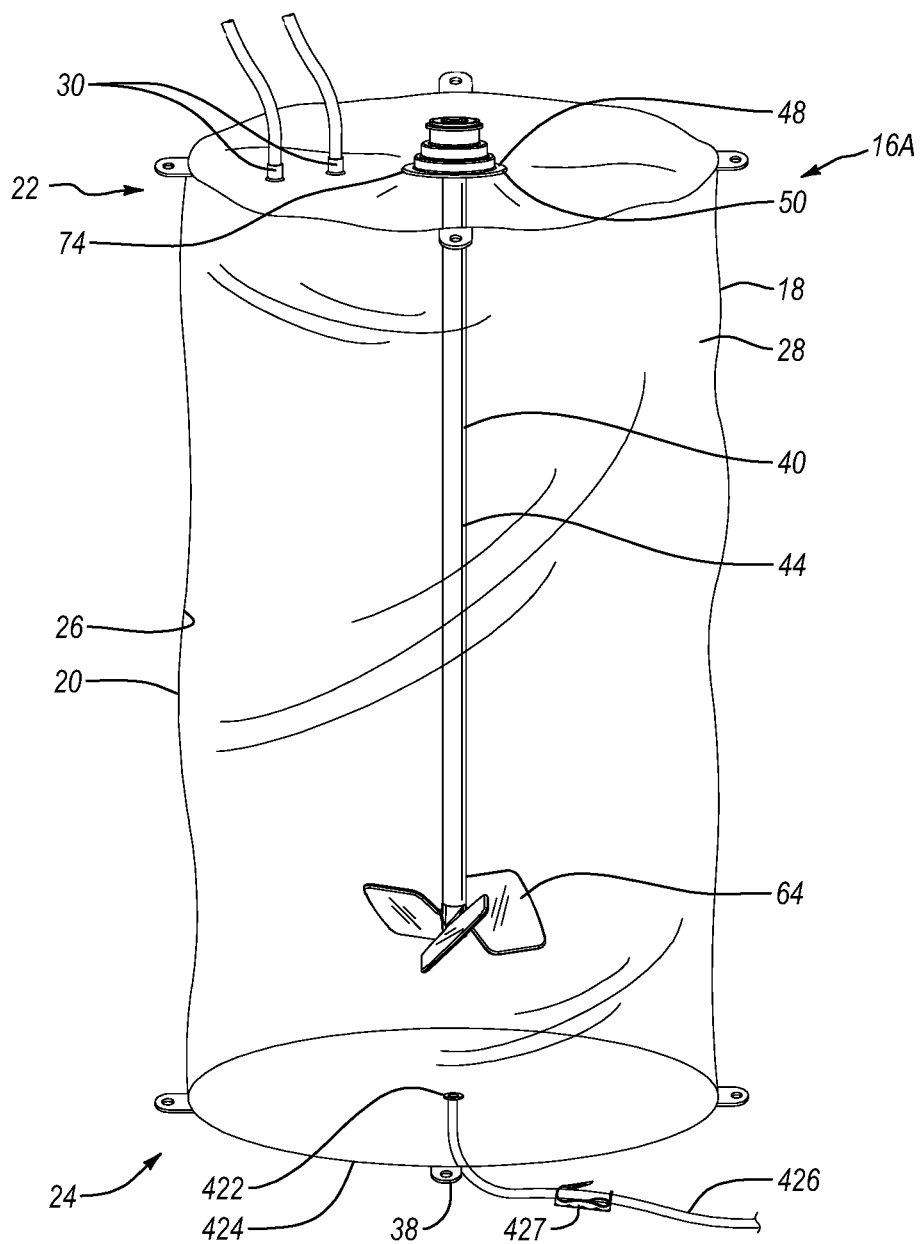
FIG. 2A is a perspective view of an alternative container assembly.

Depicted in FIG. 2A is an alternative container assembly 16A which can be used in place of container assembly 16. Container assembly 16A comprises container 18 having impeller assembly 40 attached thereto the same as in container assembly 16. However, in contrast to container assembly 16 which was designed to function as part of a fermentor or bioreactor, container assembly 16A is primarily designed for mixing and transporting fluids. As such, sparger 34 of container assembly 16 has been removed and replaced with a port 422 centrally secured on a floor 424 of container 18. A drain line 426, which is typically in the form of a flexible tube, is coupled to and extends from port 420. A hose clamp 427, as is known in the art, can be attached to drain line 426 for controlling the flow of fluid therethrough.

Returning to FIG. 1, support housing 78 has a substantially cylindrical sidewall 82 that extends between an upper end 84 and an opposing lower end 86. Lower end 86 has a floor 88 mounted thereto. As a result, support housing 14 has an interior surface 90 that bounds a chamber 92. An annular lip 94 is formed at upper end 84 and bounds an opening 96 to chamber 92. As discussed above, chamber 92 is configured to receive container assembly 16 so that container 18 is supported therein.

Although support housing 78 is shown as having a substantially cylindrical configuration, in alternative embodiments support housing 78 can have any desired shape capable of at least partially bounding a compartment. For example, sidewall 82 need not be cylindrical but can have a variety of other transverse, cross sectional configurations such as polygonal, elliptical, or irregular. Furthermore, it is appreciated that support housing 78 can be scaled to any desired size. For example, it is envisioned that support housing 78 can be sized so that chamber 92 can hold a volume of less than 50 liters, more than 1,000 liters or any of the other volumes or range of volumes as discussed above with regard to container 18. Support housing 78 is typically made of metal, such as stainless steel, but can also be made of other materials capable of withstanding the applied loads of the present invention.

It is appreciated that floor 88 of support housing 78 can be formed with a central opening extending therethrough for gas line 36 (FIG. 2) to pass. In addition, any desired number of openings can be formed through sidewall 82 at lower end 86 to permit access to ports 31 (FIG. 2). One or more larger openings that are closed by a door can also be formed through sidewall 82 at lower end 86. The larger openings enable an operator to reach into chamber 92 for aligning container 18 and passing gas line 36 (FIG. 2) through the floor opening.

In one embodiment of the present invention, means are provided for controlling the temperature of the fluid within container 18 when container 18 is disposed within support housing 78. As one example of the means, support housing 78 is jacketed having a fluid inlet 184 and a fluid outlet 186. The jacket enables heated or cooled fluid to pass through support housing 78 for controlling the temperature of the fluid within container 18. In an alternative embodiment, electrical heating elements can be mounted on or within support housing 78. Alternatively, the temperature can be controlled by applying gas burners to support housing 78 or pumping the fluid out of container 18, heating the fluid and then pumping the fluid back into container 18.

Further discussion with regard to openings that can be formed on support housing 78, the jacketing of support housing 78 and other alternative features for support housing 78 are disclosed in US Patent Publication No. US 2011/0310696 A1, published Dec. 22, 2011 which is incorporated herein by specific reference.

As also depicted in FIG. 1, cart 80A comprises a platform 190 having a top surface 192 and an opposing bottom surface 194. In the depicted embodiment, platform 190 has a substantially square configuration. In alternative embodiments, however, platform 190 can be triangular, rectangular, circular, or of other polygonal or irregular configurations. Downwardly projecting from bottom surface 194 are a plurality of spaced apart wheels 196. A plurality of spaced apart legs 198 extend between floor 88 of support housing 78 and top surface 192 of platform 190. Legs 198 provide an open gap between support housing 78 and platform 190 so as to enable access to floor 88. In other embodiments, cart 80A can be eliminated and support housing 78 can be supported by legs 198 on a ground or floor surface or on a pallet or other support structure.

Figure 4:
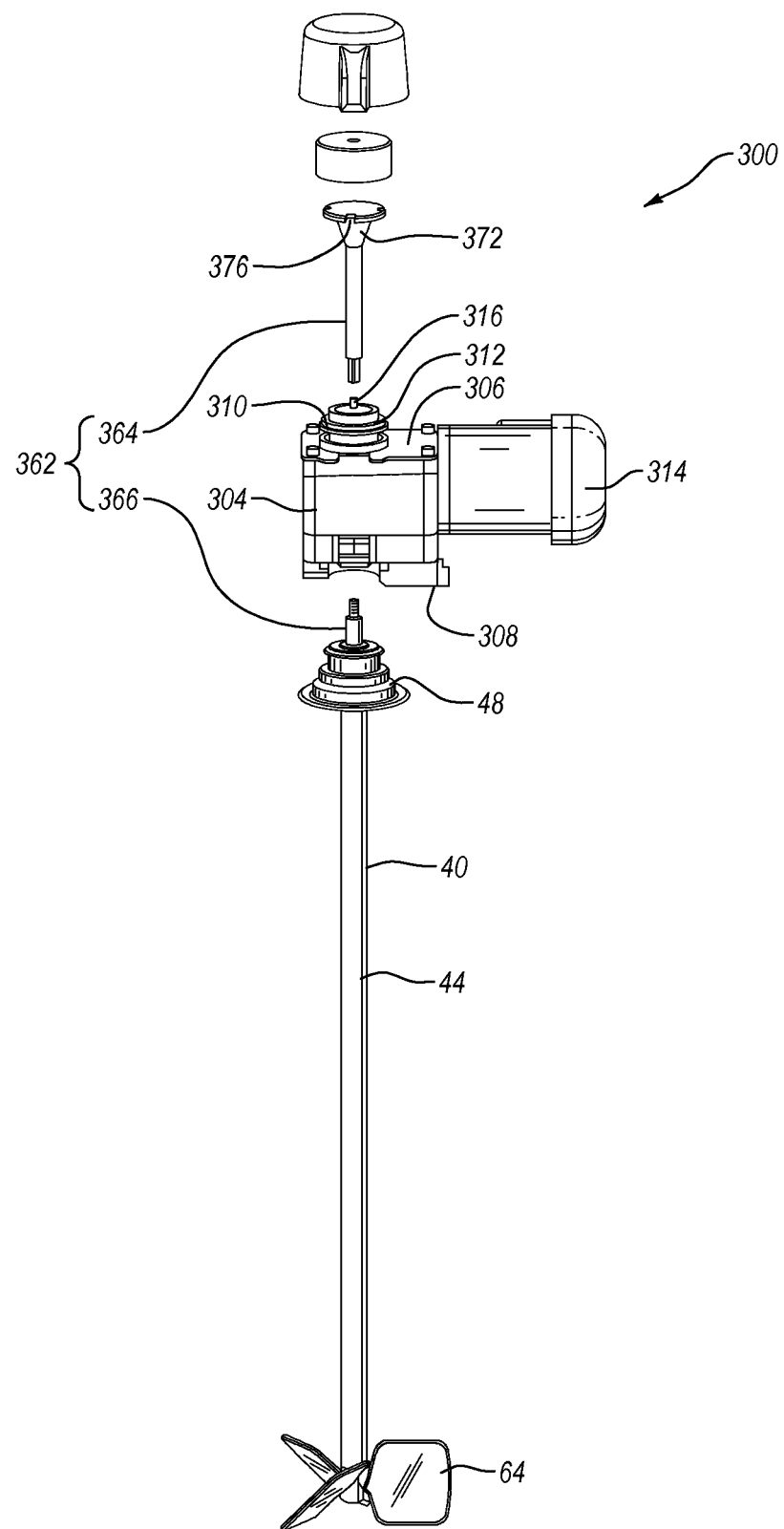
FIG. 4 is a partially disassembly perspective view of a drive motor assembly of the fluid mixing system shown in FIG. 1 in association with the impeller assembly and drive shaft of FIG. 3.

As also shown in FIG. 1, drive motor assembly 300 is coupled with support housing 78 by adjustable arm assembly 302A. Drive motor assembly 300 is used in conjunction with drive shaft 362 (FIG. 3) and can be used for mixing and/or suspending a culture or other solution within container 18 (FIG. 2). Turning to FIG. 4, drive motor assembly 18 comprises a housing 304 having a top surface 306 and an opposing bottom surface 308. An opening 310 extends through housing 304 from top surface 306 to bottom surface 308. A tubular motor mount 312 is rotatably secured within opening 310 of housing 304. Upstanding from motor mount 312 is a locking pin 316. A drive motor 314 is mounted to housing 304 and engages with motor mount 312 so as to facilitate select rotation of motor mount 312 relative to housing 304. Drive shaft 362 is configured to pass through motor mount 312 so that engaging portion 372 of drive shaft 362 is retained within motor mount 312 and locking pin 316 of motor mount 312 is received within notch 376 of drive shaft 362. As a result, rotation of motor mount 312 by drive motor 314 facilitates rotation of drive shaft 362. Further discussion of drive motor assembly 300 and how it engages with drive shaft 362 and alternative designs of drive motor assembly 300 are discussed in US Patent Publication No. US 2011/0188928 A1, published Aug. 4, 2011 which is incorporated herein by specific reference.

Figure 5:
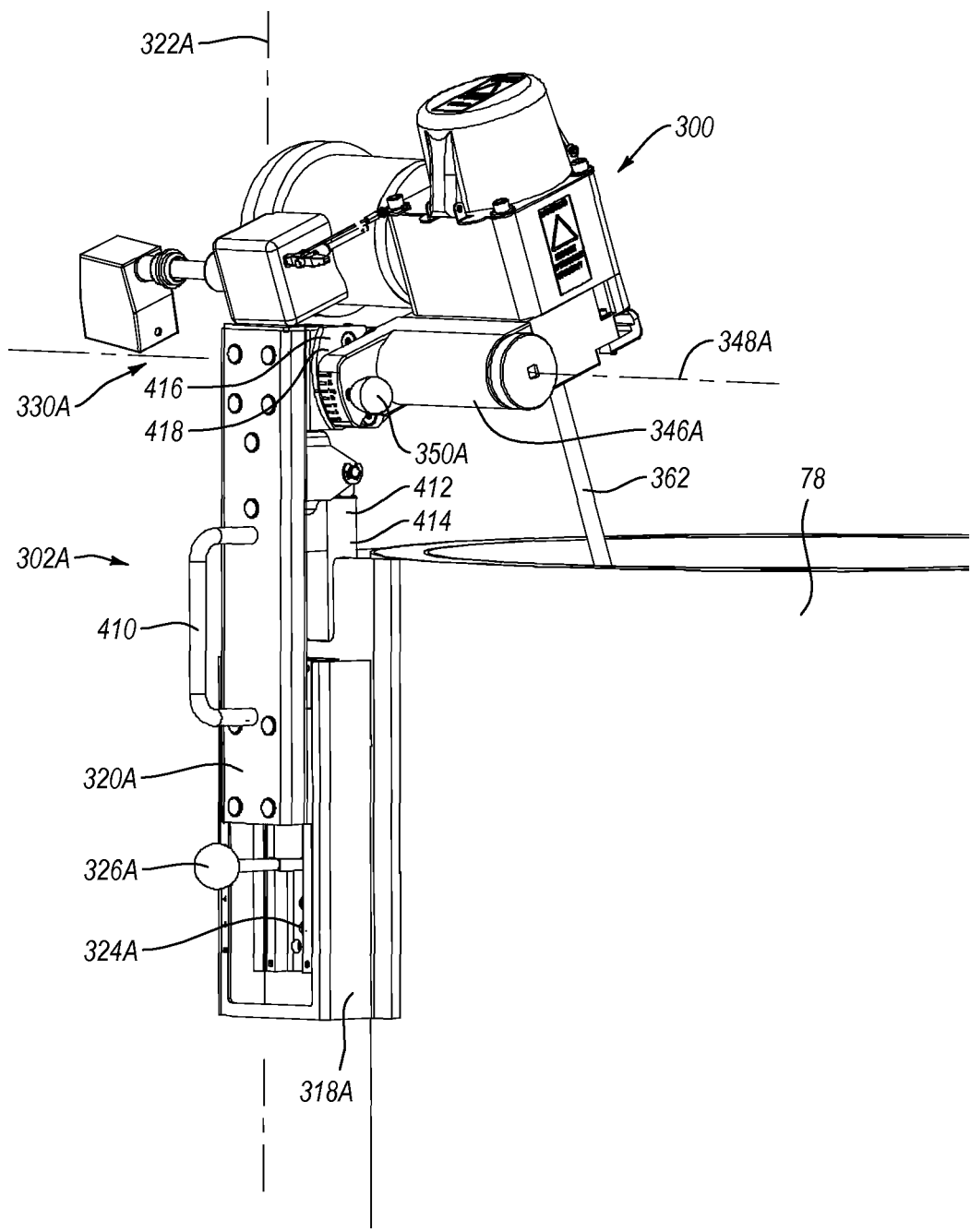
FIG. 5 is a right side perspective view of the adjustable arm assembly of the mixing system shown in FIG. 1.
Figure 6:
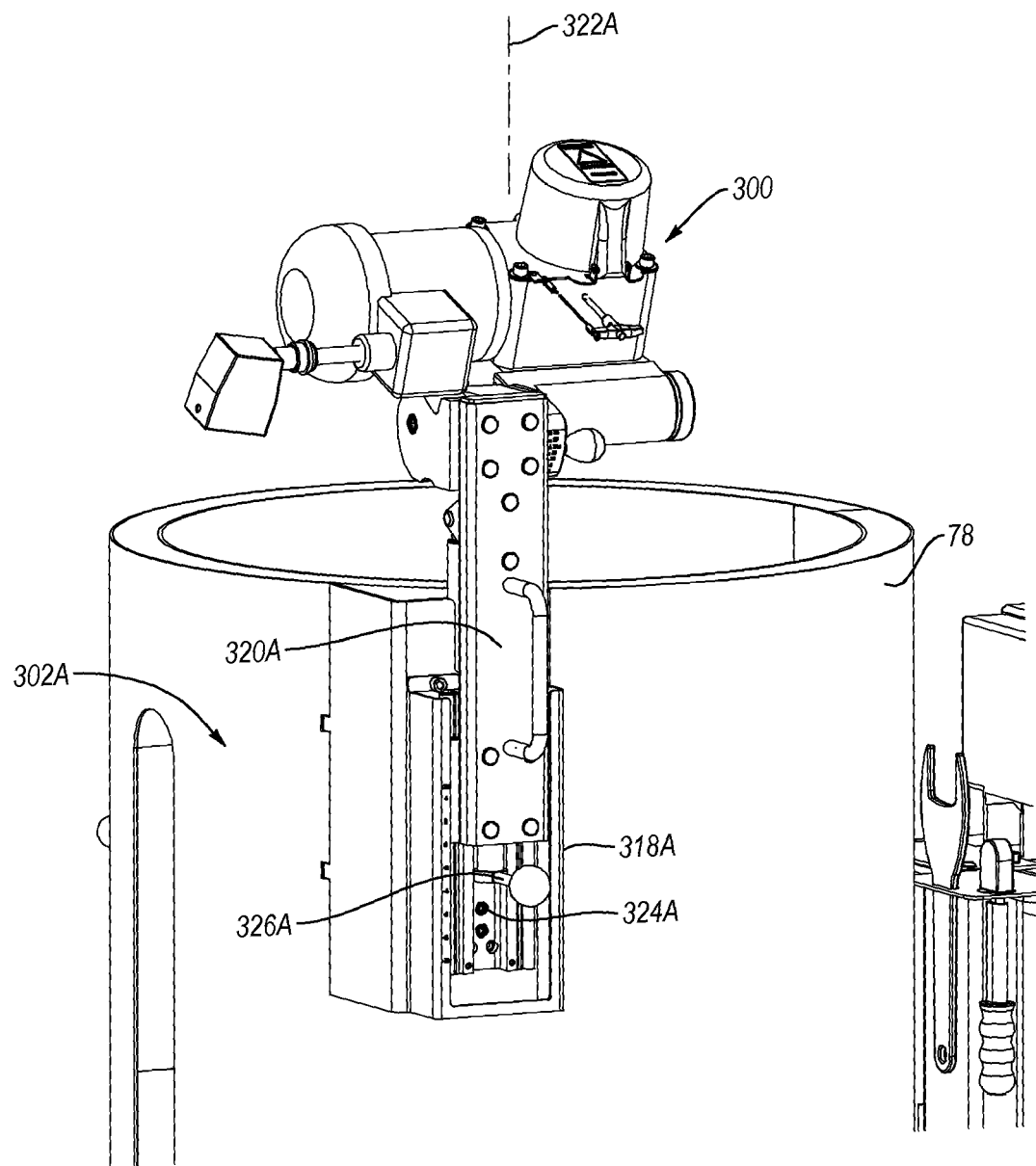
FIG. 6 is a left side perspective view of the adjustable arm assembly shown in FIG. 5.

Continuing with FIG. 1, arm assembly 302A is used to adjust the position of drive motor assembly 300 and thereby adjust the position of drive shaft 362 (FIG. 5) and impeller 64 (FIG. 2) mounted on the end thereof. As mentioned above and as will be discussed below in greater detail, the ability to adjust the position of impeller 64 enables optimal mixing of fluid within container 18. As depicted in FIG. 1, arm assembly 302A comprises a first housing 318A that is rigidly secured to upper end 84 of support housing 78. As shown in FIGS. 5 and 6, slidably coupled with first housing 318A is an elongated first support 320A. A handle 410 is mounted to first support 320A for use in manually raising and lowering first support 320A. First housing 318A and first support 320A are orientated such that first support 320A can slide vertically up and down along a first axis 322A. In an alternative embodiment, first housing 318A and first support 320A can be disposed so that axis 322A is disposed at an angle in a range between 0° to about 30° relative to vertical. Other angles can also be used.

In one embodiment of the present invention, means are provided for selectively locking first support 320A to first housing 318A at different locations along axis 322A. In one embodiment of the present invention as shown in FIG. 6, such means comprises holes 324A formed at spaced apart locations along first housing 318A and a spring activated pin 326A mounted to first support 320A. By pulling out pin 326A, first support 320A is free to slide vertically up and down along axis 322A. By releasing or pushing in pin 326A, pin 326A is received within a corresponding hole 324A so as to lock first support 320A in place. It is appreciated that any number of conventional clamps, pins, screws, latches, fasteners, or the like can be used for securing first support 320A to first housing 318A. Indicia or markings can be formed along the surface of first support 320A and/or first housing 318A to indicate the relative position of first support 320A.

Returning to FIG. 5, in one embodiment a lift assist 412 is provided for assisting in raising and lowering first support 320A and drive motor assembly 300. In the depicted embodiment, lift assist 412 comprises a cylinder 414 having a first end pivotably coupled with the upper end of first support 320A and an opposing second end pivotably coupled with the lower end of first housing 318A or with support housing 78. Cylinder 412 is resiliently compressible. For example, cylinder 412 can comprise two nested cylinders halves having a spring or compressible gas disposed therebetween. Cylinder 412 is positioned so that when first support 320A is lowered, cylinder 412 is resiliently compresses so that the produced resilient force can subsequently be used to assist the operator in raising first support 320A and drive motor assembly 300. Lift assist 412 thus permits an operator to easily and smoothly raise and lower first support 320A with drive motor assembly 300 mounted thereon. In other embodiments, it is appreciated that lift assist 412 can be automated to raise and lower first support 320A by activating a switch or through the use of a controller. In those embodiments, lift assist 412 can be operated through the use of an electrical motor or through use of pneumatic or hydraulic systems.

First support 320A terminates at an upper end 330A. Mounted on upper end 330A is a frame 416 having a side face 418. A second support 346A is rotatably mounted to side face 418 of frame 416. Second support 346A is mounted so that it rotates about a second axis 348A relative to frame 416. Second axis 348A can be disposed in a horizontal plane or at an angle in a range between about 0° to about 30° relative to the horizontal. Axis 348A can thus be perpendicular to axis 322A. Drive motor assembly 300 is secured to second support 346A such that rotation of second support 346A facilitates concurrent rotation of drive motor assembly 300.

One embodiment of the present invention also includes means for locking second support 346A at different angles about second axis 348A. By way of example and not by limitation, a spring activated pin 350A is mounted on an arm of second support 346A. When pin 350A is retracted, second support 346A is free to rotate about second axis 348A. As pin 350A is released or advanced inward, pin 350A is received within one of a plurality of holes formed on side face 418 of frame 416. As a result, second support 346A is thereby precluded from further rotation. Other conventional fastening techniques can also be used. In other embodiments, it is appreciated that second support 346A can be automated to rotate by activating a switch or through the use of a controller such as discussed above with regard to lift assist 412.

In view of the foregoing, first support 320A can facilitate vertical movement of drive motor assembly 300 while second support 346A can facilitate tilting of drive motor assembly 300. Because drive shaft 362 and impeller 64 move concurrently and proportionally with drive motor assembly 300, adjustable arm assembly 302A can thus be used to selectively position the vertical height and tilt of impeller 64.

Figure 7:
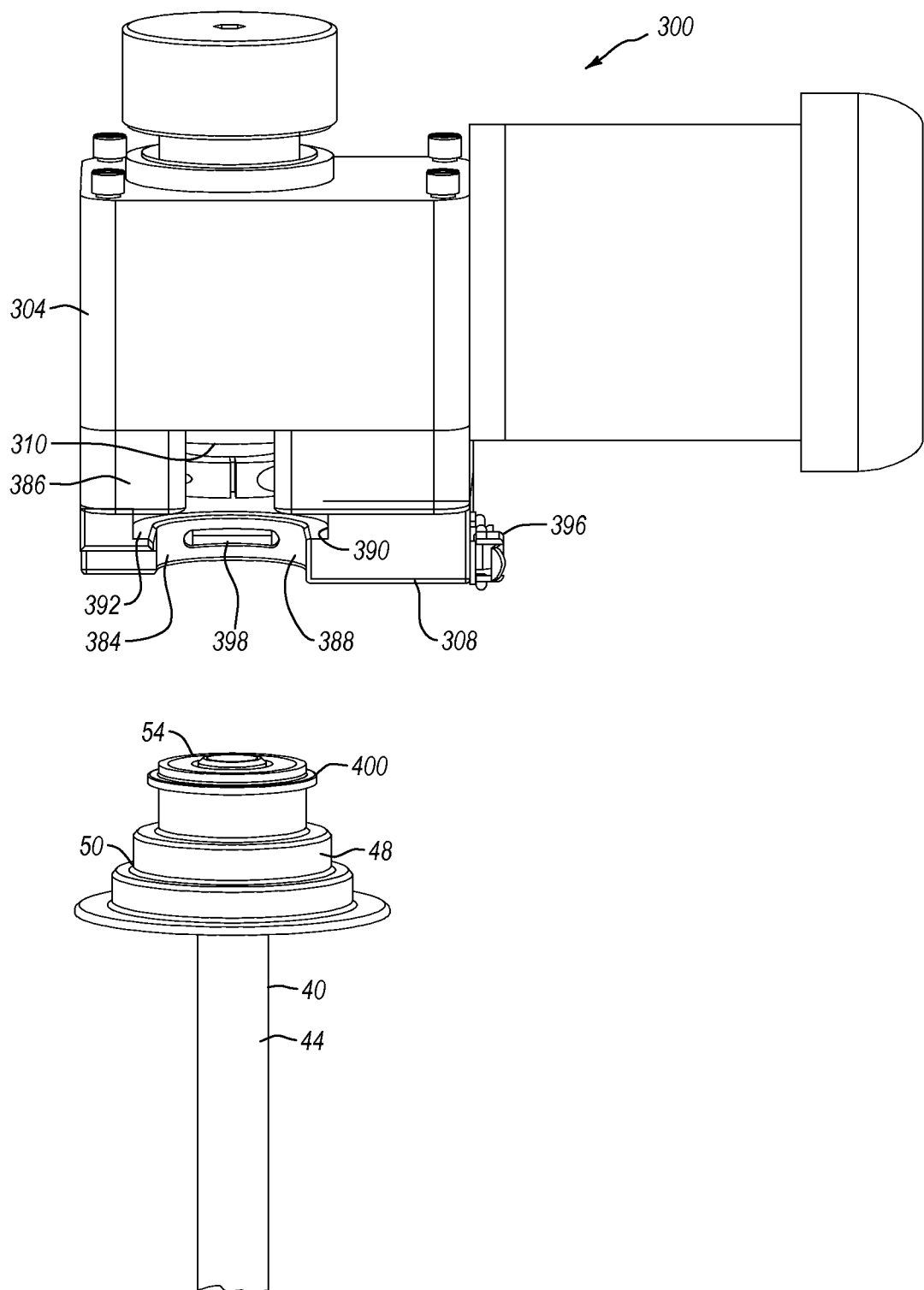
FIG. 7 is a front perspective view of the drive motor assembly and rotational assembly.

During use, arm assembly 302A is used to properly position drive motor assembly 300 so that rotational assembly 48 (FIG. 2) can be coupled with drive motor assembly 300. Specifically, as depicted in FIG. 7, housing 304 of drive motor assembly 300 has an open access 384 that is recessed on a front face 386 so as to communicate with opening 310 extending through housing 304. Access 384 is in part bounded by a substantially C-shaped first side wall 388 that extends up from bottom surface 308, a concentrically disposed substantially C-shaped second side wall 390 disposed above first side wall 388 and having a diameter larger than first side wall 388, and a substantially C-shaped shoulder 392 extending between side walls 388 and 390. As shown in FIG. 2, a door 394 is hingedly mounted to housing 304 and selectively closes the opening to access 384 from front face 386. Returning to FIG. 7, door 394 is secured in a closed position by a latch 396. Positioned on first side wall 388 is a section 398 of a resilient and/or elastomeric material such as silicone. Other sections 398 of similar materials can also be positioned on first side wall 388 or the interior surface of door 394.

Figure 8:
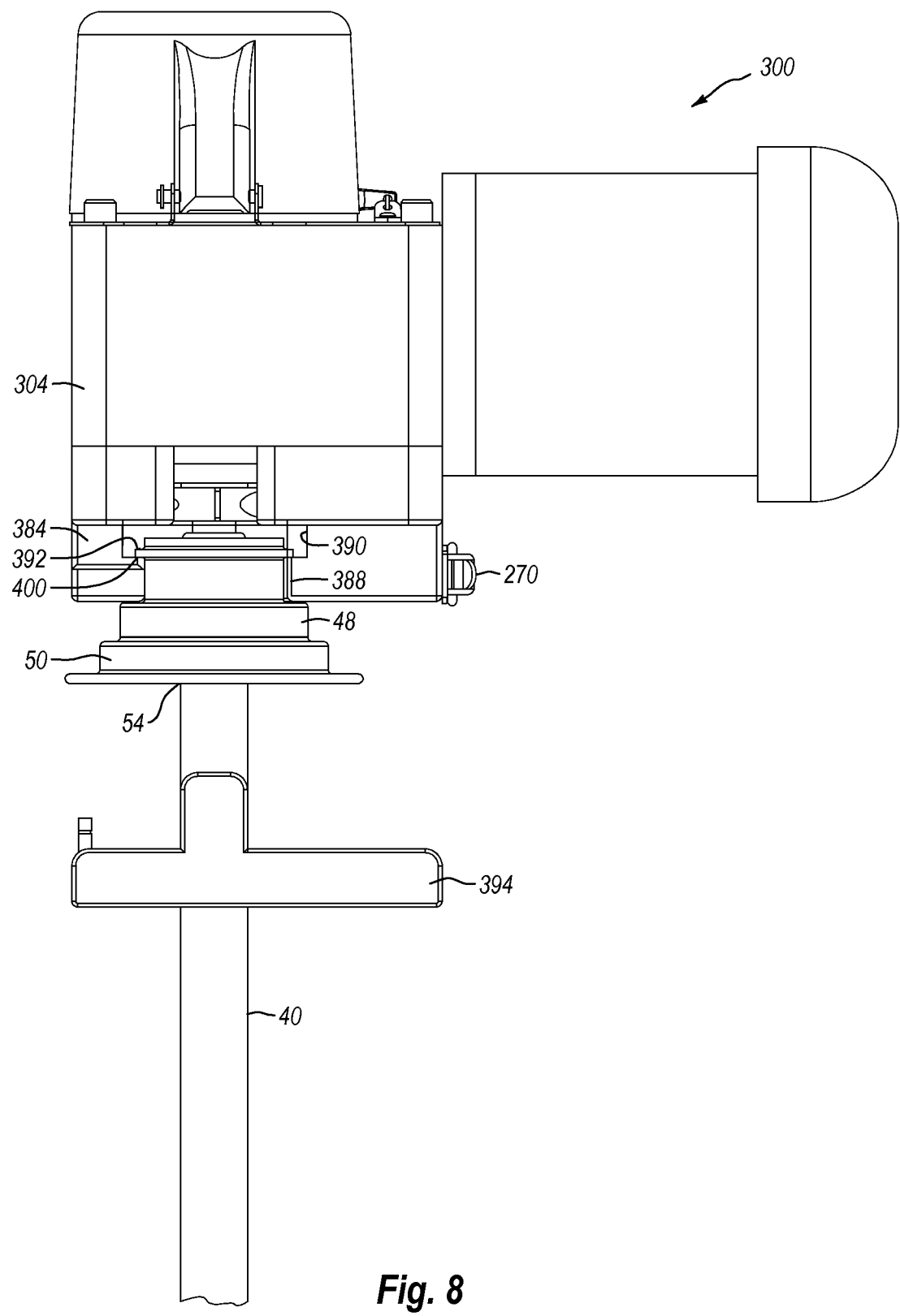
FIG. 8 is an elevated front view of the rotational assembly shown in FIG. 7 coupled with the drive motor assembly.

As depicted in FIG. 8, to facilitate attachment of rotational assembly 48 to housing 304, with door 394 rotated to an open position, rotational assembly 48 is horizontally slid into access 384 from front face 386 of housing 304 so that a support flange 400 radially outwardly extending from an upper end of rotational assembly 48 rests on shoulder 392 of access 384. Rotational assembly 48 is advanced into access 384 so that the passage extending through hub 54 of rotational assembly 48 aligns with the passage extending through motor mount 312 (FIG. 4). In this position, door 394 is moved to the closed position and secured in the closed position by latch 396. As door 394 is closed, casing 50 of rotational assembly 48 is biased against the one or more sections 398 (FIG. 7) of resilient material so as to clamp rotational assembly 48 within access 384 and thereby prevent unwanted rotational movement of casing 50 relative to housing 304 of drive motor assembly 300.

Once rotational assembly 48 is secured to drive motor assembly 300, drive shaft 362 (FIG. 2) can be advanced down through drive motor assembly 300 and into impeller assembly 40 so as to engage impeller 64. Once drive shaft 362 is properly positioned, drive motor assembly 300 is activated causing drive shaft 362 to rotate impeller 64 and thereby mix or suspend the fluid within container 18. When the processing is complete, drive shaft 362 is removed and rotational assembly 48 is separated from drive motor assembly 300.

One advantage of being able to selectively adjust the vertical height and tilt of impeller 64 through the use of arm assembly 302A is that mixing assembly 10A can be used to maintain optimal mixing conditions of fluid within a single container assembly 16 over a relatively large change in fluid volumes. Specifically, the preferred position for impeller 64 within container 18 to achieve optimal mixing can be determined using conventional techniques. This position can be measured as a height from the bottom of container assembly 16 and is subject to the height of the fluid within container assembly 16. Thus, as the fluid level increases within container assembly 16, the height of the location for impeller 64 to achieve optimal mixing also increases and vice-a-versa. Maintaining impeller 64 at the optimal location of mixing helps to ensure that the fluid is homogeneous. This can be especially helpful where mixing system 10A is functioning as a bioreactor or fermentor. In that case, the media, additives, and cells or microorganism should be continually turned over and homogeneously dispersed to ensure that all of the cells and microorganism are being continuously and uniformly fed and oxygenated.

It is also common that the volume of fluid within container assembly 16 will vary significantly. For example, when first starting a bioreactor or fermentor, the seed inoculum of cells or microorganisms can be dispersed into a rather small volume of media within container assembly 18. As the cells/microorganisms grow and multiple, more media and additives can be progressively added to container assembly 16. By using the inventive system, the seed inoculum can be delivered into a relatively large container assembly 16 although only a small volume of media is initially being used. In this initial step, impeller 64 is lowered to achieve optimal mixing of the initial volume. As more fluid is progressively added into container 18, impeller 64 is progressively raised to maintain optimal mixing for the defined fluid volume. When the culturing is complete or it is otherwise desired to remove the solution or suspension from container assembly 16, impeller 64 can again be progressively lowered as the fluid within container assembly 16 is progressively lowered. During the mixing process, it is typically preferred to maintain a positive gas pressure within container assembly 16, such as in a range from 0.05 psi to about 2 psi to keep container assembly 16 away from the rotating impeller assembly 40 and to keep container 18 against heated support housing 78 to maintain temperature regulation. This can be more important during low volume processing.

The ability to progressively add and remove relatively large amounts of fluid from a single container while maintaining optimal mixing of the fluid eliminates or at least decreases the need to transfer the solution to different sized containers for processing. By using a single container for processing as opposed to moving the fluid between different sized containers, the inventive system decreases processing down time, avoids the expense of unnecessary containers, minimizes the risk of contamination, and minimizes potential damage to cells/microorganisms. The inventive system can operate over a relatively high turn-down ratio. A "turn-down ratio" is the ratio of maximum to minimum volumes of fluid that a single container can process while maintaining acceptable mixing conditions. For example, a turn-down ratio of 10:1 means that if the initial volume that a mixing system can process at acceptable mixing conditions is 10 liters, the volume of fluid with the container can be increased by a factor of 10, i.e., up to 100 liters, and the system would still be able to process the fluid at acceptable mixing conditions. By using inventive mixing system 10A as a bioreactor, fermentor, or other system that requires mixing or suspension it is appreciated that containers assembly 16 can be sized to operate with a turn-down ratio of at least 5:1, 10:1, 15:1, 20:1 or ranges therebetween.

What constitutes acceptable mixing conditions is in part dependent upon what is being processed. When the system is functioning as a bioreactor or fermentor growing cells or microorganisms, the mixing should, in general, assist in dispersal of the cells/microorganisms and sparged gas throughout the solution so that the cells/microorganisms has access to the required nutrients in the media and proper mass transfer is achieved with the sparged gas. However, the mixing should not be so sever as to apply unwanted shear forces to the cells/microorganisms, create undesired splashing, or cause cavitation or a vortex in the solution, all of which can hamper the growth of cells/microorganisms.

In alternative embodiments, it is appreciated that adjustable arm assembly 302A can have a variety of different configurations. For example, adjustable arm assembly 302A can be modified to permit select lateral displacement of drive shaft 362 and impeller 64 that is independent of tilting or vertical displacement. In addition, the adjustable arm assembly can be mounted on a separate docking station that removably couples with support housing 78. One specific example of such an adjustable arm assembly is disclosed in US Patent Publication No. US 2011/0310696 A1, published Dec. 22, 2011 which is incorporated herein by specific reference. One benefit of this design is that a single adjustable arm assembly can be used with multiple different support housings and particularly with support housings have different height and diameter sizes. For container assemblies 16 having different sized diameters, impeller 64 may need to be adjusted laterally so that impeller 64 is centrally positioned to achieve optimal mixing. In other situations, lateral displacement may be desirable to permit mixing closer to or father away from the wall of container 18.

Figure 9:
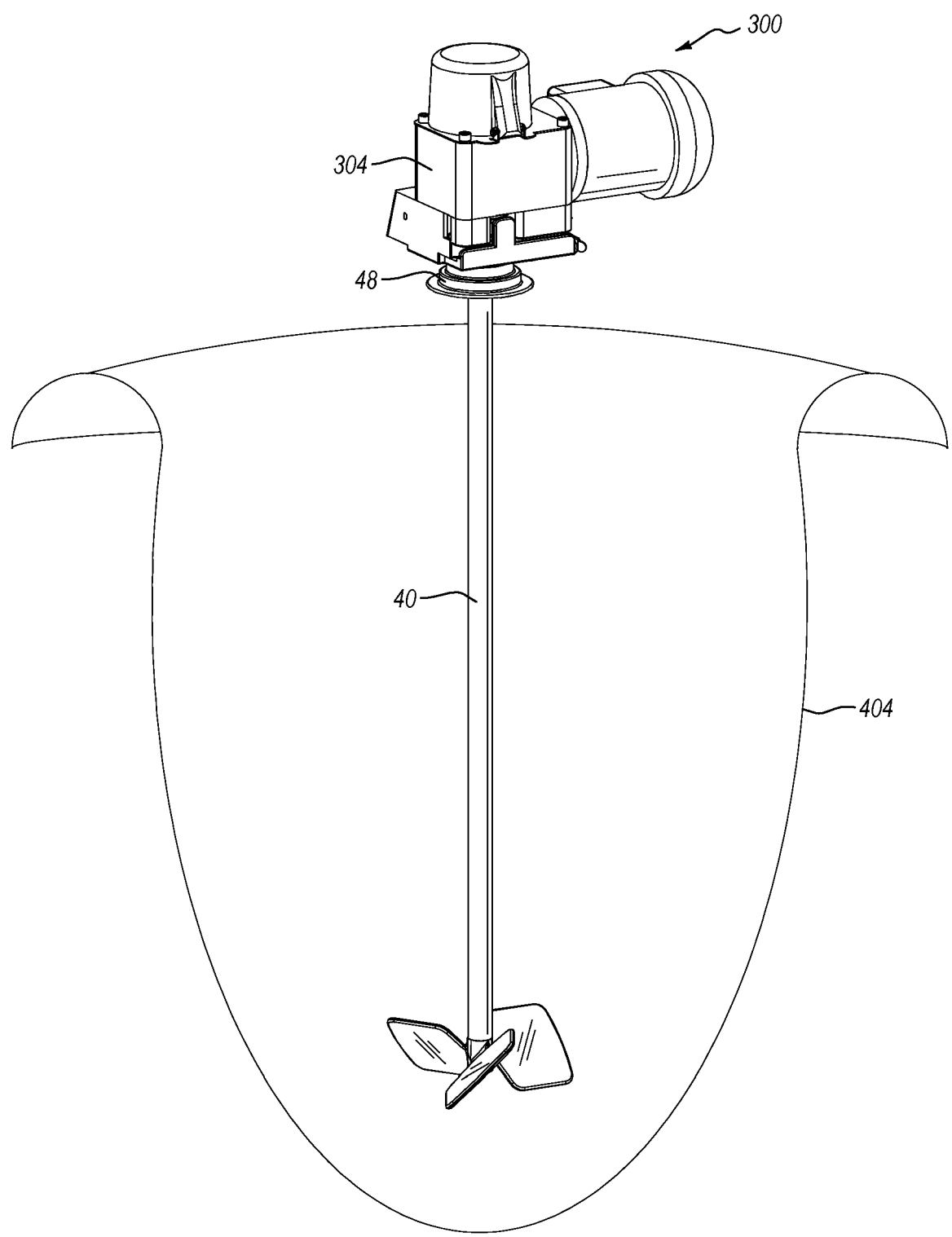
FIG. 9 is a perspective view of an alternative embodiment of a container being used with a drive motor assembly and impeller assembly.
Figure 10:
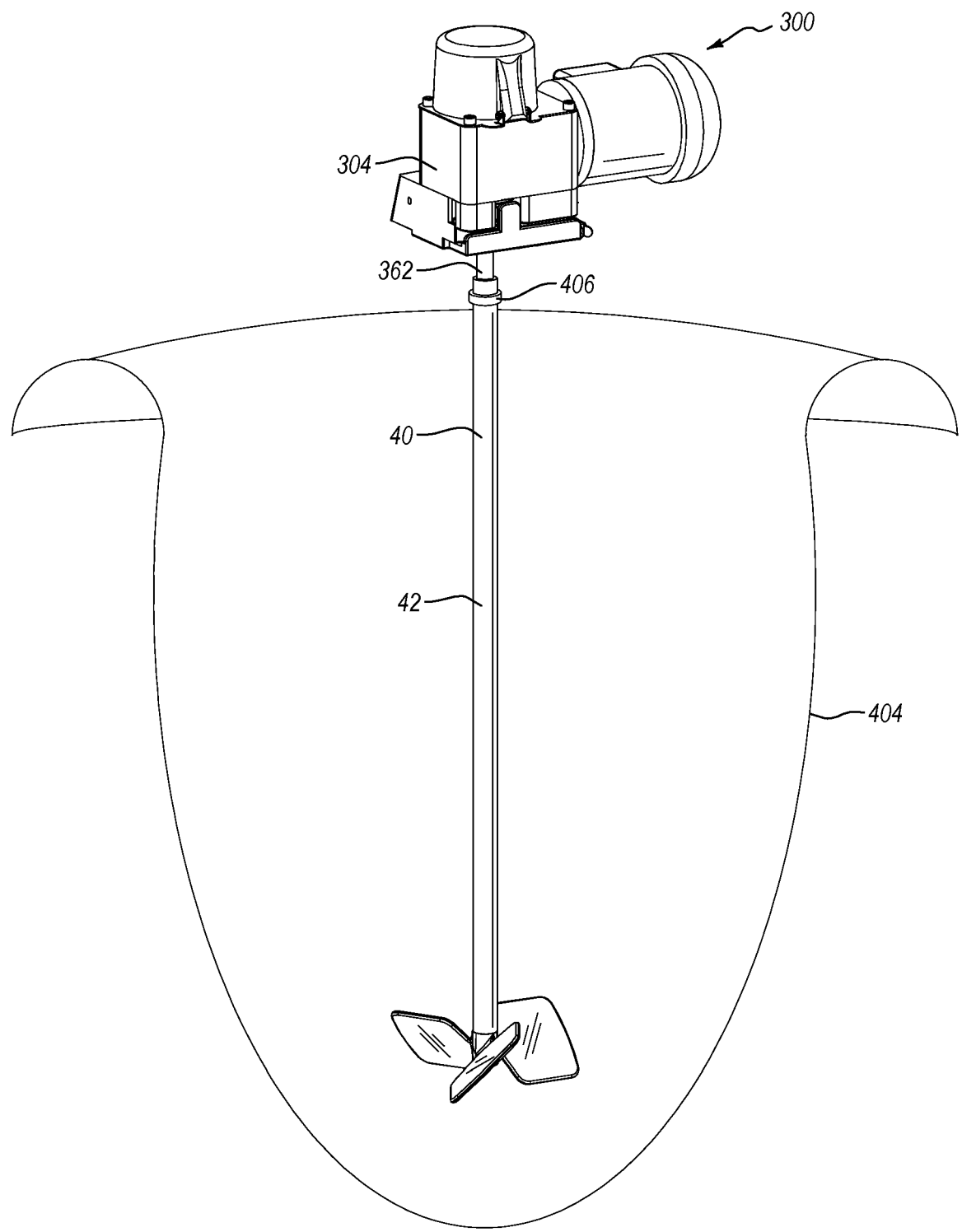
FIG. 10 is a perspective view of an alternative embodiment of the impeller assembly shown in FIG. 9.

Depicted in FIG. 9 is another alternative embodiment of the present invention wherein like elements are identified by like reference characters. In this embodiment drive motor assembly 300 operates with a container 404 that is an open top liner. Container 404 is positioned within chamber 92 of support housing 78 so that is drapes over annular lip 94 (FIG. 1). This configuration can be used as a lower cost alternative for mixing non-sterile fluids. In this embodiment, rotational assembly 48 merely functions to secure impeller assembly 40 to drive motor assembly 300 so that it does not unintentionally slide off of drive shaft 362. In alternative embodiments, because rotational assembly 48 is no longer forming a sealed fluid connection with the container, rotational assembly 48 can be substantially simplified. For example, as shown in FIG. 10, rotational assembly 48 can be replaced by a clamp 406 that secures tubular connector 44 to drive shaft 362. Further alternative embodiments with regard to impeller assembly 40 and how they can be attached to drive motor assembly 300 or drive shaft 362 are discussed in US Patent Publication No. US 2011/0188928 A1, published Aug. 4, 2011 which is incorporated herein by specific reference.

Figure 11:
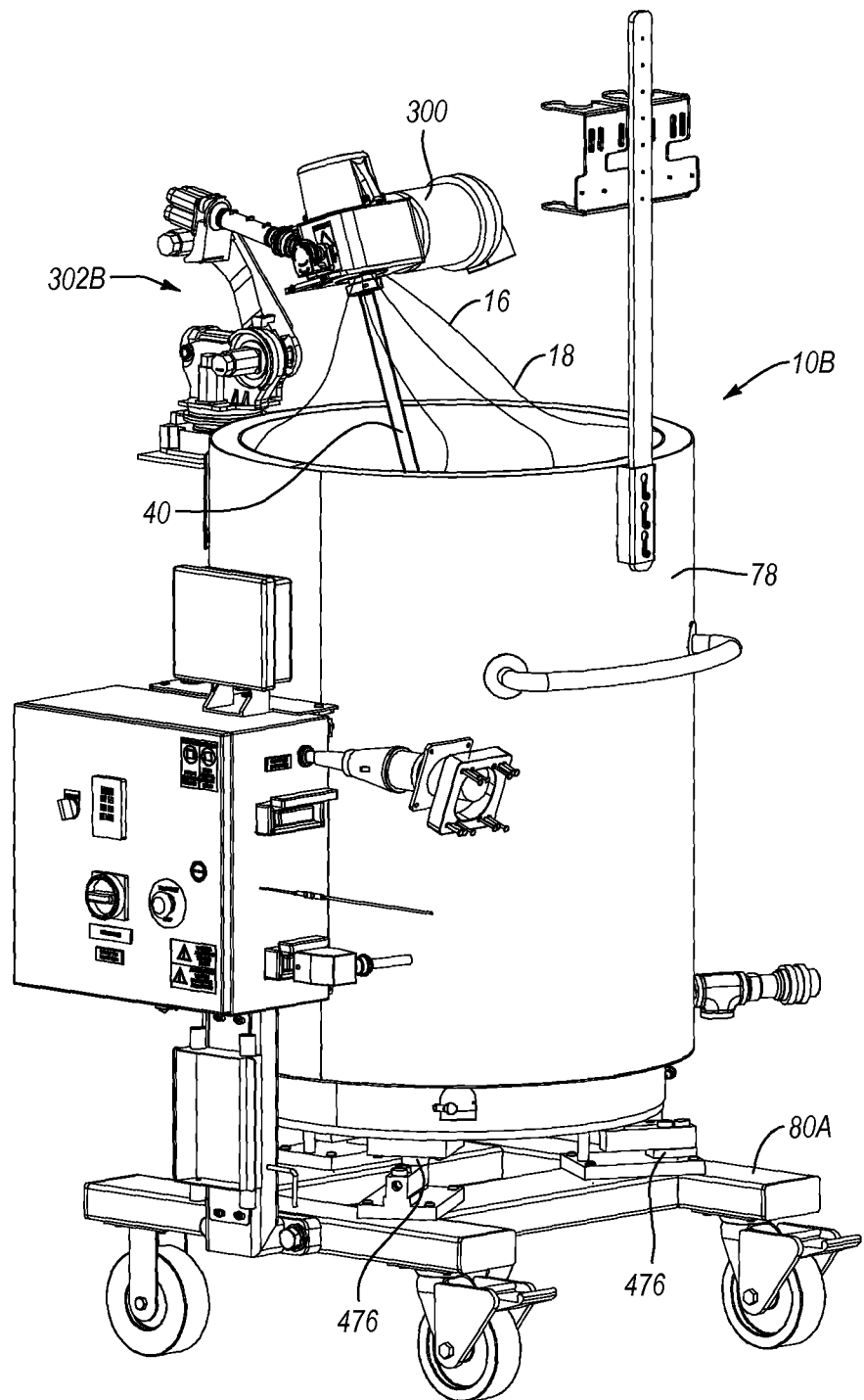
FIG. 11 is a perspective view of another alternative embodiment of a mixing system incorporating features of the present invention.

Depicted in FIG. 11 is another alternative embodiment of an inventive mixing system 10B incorporating features of the present invention. Like elements between systems 10A and 10B are identified by like reference characters. In general, mixing system 10B comprises support housing 78, cart 80A on which on which support housing 78 rests, drive motor assembly 300, an adjustable arm assembly 302B which supports drive motor assembly 300, container assembly 16 that is supported within support housing 78, and drive shaft 362 (FIG. 12) that extends between drive motor assembly 300 and impeller assembly 40 of container assembly 16. The primary difference between mixing systems 10A and 10B is the modification of adjustable arm assembly 302B relative to adjustable arm assembly 302A.

Figure 12:
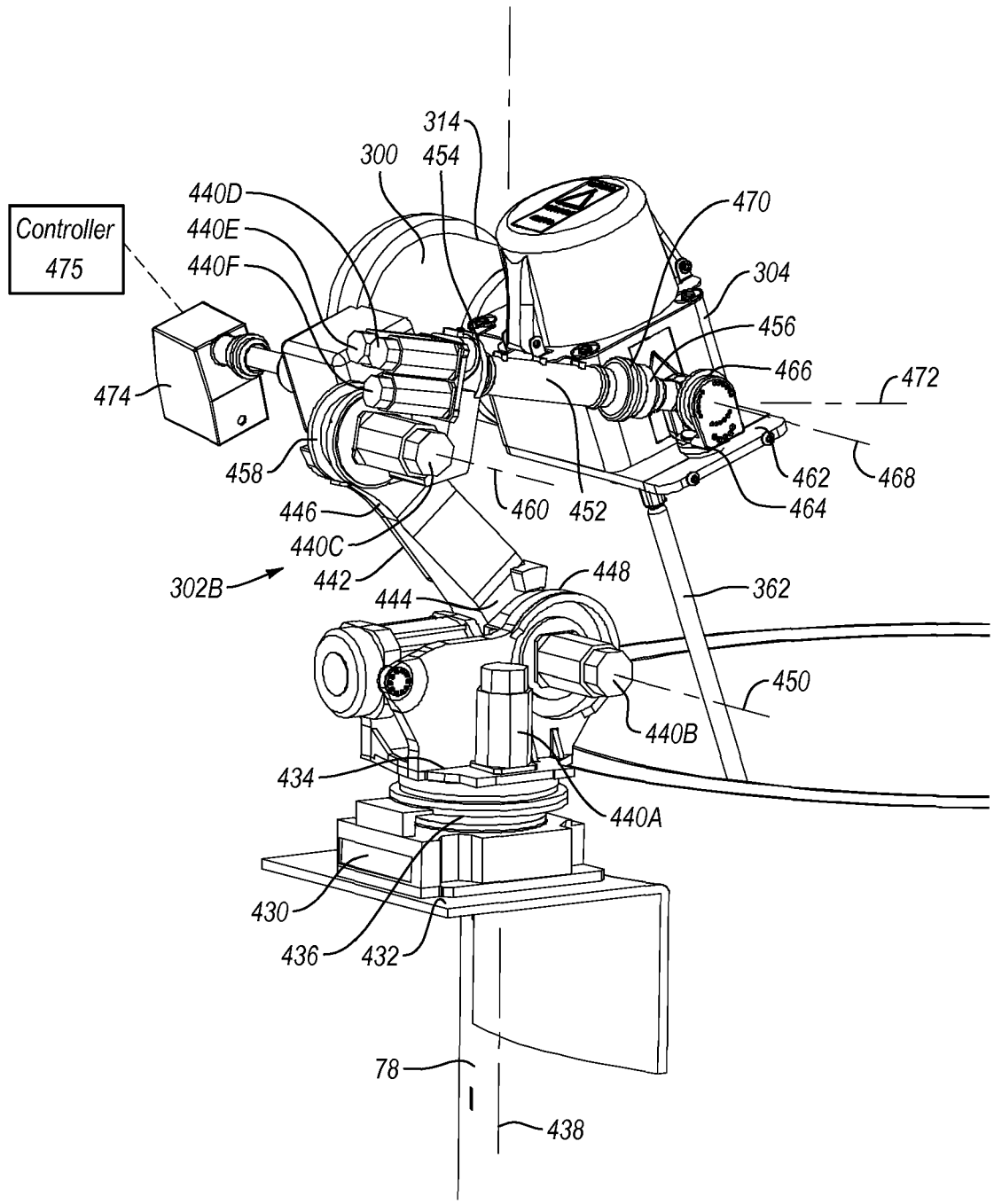
FIG. 12 is a right side perspective view of the adjustable arm assembly of the mixing system shown in FIG. 11.
Figure 13:
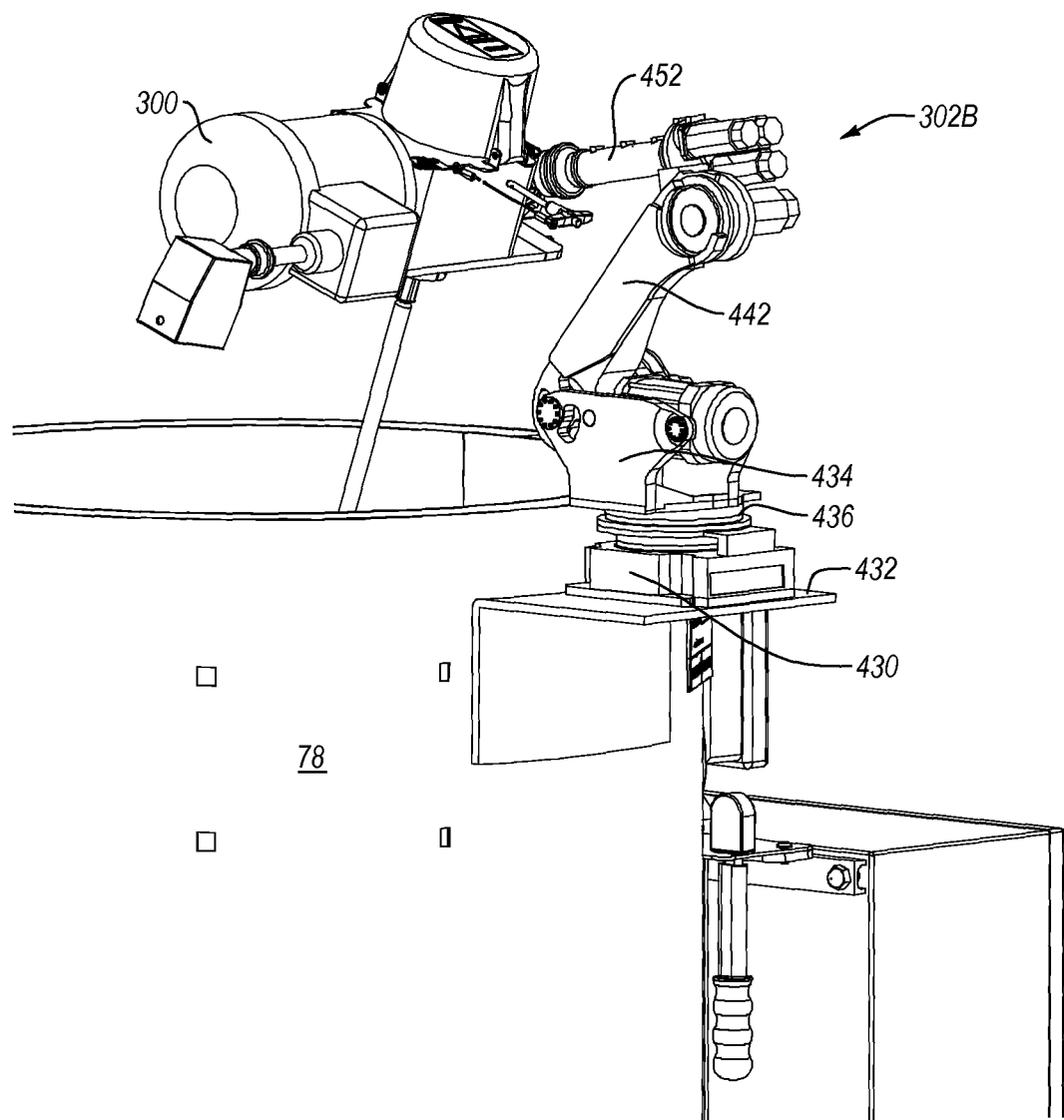
FIG. 13 is a left side perspective view of the adjustable arm assembly shown in FIG. 12.

As depicted in FIGS. 12 and 13, adjustable arm assembly 302B is in the form of a programmable robotic arm having multiple axes of rotation that enable the robotic arm to periodically or continuously adjust the position of impeller 64 three dimensionally, including tilting of impeller 64. Specifically, adjustable arm assembly 302B includes a lower base 430 that is mounted on a support platform 432 projecting from supporting housing 78. An upper base 434 is mounted on lower base 430 by a first swivel joint 436. First swivel joint 436 permits upper base 434 to rotate relative to lower base 432 about a first axis 438 that is vertically oriented or can be offset from vertical over an angel in a range from about 0° to about 30°. A first motor 440A is mounted on upper base 434 and engages with first swivel joint 436 for controlling rotation of upper base 434 about first axis 438.

Mounted to upper base 434 is a first arm 442 having a first end 444 and an opposing second end 446. First end 444 is rotatably mounted to upper base 434 by a second swivel joint 448. Second swivel joint 448 rotates about a second axis 450 that is horizontally disposed and/or extends perpendicular to first axis 438. A second motor 440B engages with second swivel joint 448 for controlling rotation of first end 444 of first arm 442 about second axis 450.

Arm assembly 302B also includes a second arm 452 having a first end 454 and an opposing second end 456. First end 454 of second arm 452 is rotatably mounted to second end 446 of first arm 442 by way of a third swivel joint 458. Third swivel joint 458 rotates about a third axis 460 that is also horizontally disposed and/or is parallel to second axis 450. A motor 440C engages third swivel joint 458 for controlling rotation of first end 454 of second arm 452 about third axis 460.

Drive motor assembly 300 is rotatably coupled to second end 456 of second arm 452. Specifically, a flange 462 projects out from a side of housing 304 of drive motor assembly 300. Secured to flange 462 is a mount 464. Second end 456 of second arm 452 is rotatably mounted to mount 464 by a fourth swivel joint 466. Fourth swivel joint 466 rotates about a fourth axis 468 which is also horizontally disposed and/or is parallel to axis 450 and 460. A motor 440D is shown mounted at first end 454 of second arm 452 and is operably coupled with fourth swivel joint 466 for controlling rotation of drive motor assembly 300 about fourth axis 468. In alternative embodiments, it is appreciated that motor 440 can be secured to mount 464.

In one embodiment, a fifth swivel joint 470 can be formed on second arm 452 at a location between opposing ends 454 and 456. Swivel joint 470 rotates about a fifth axis 472 that centrally extends along the length of second arm 452 and extends orthogonal to axis 460 and 468. Motor 440E is disposed at first end 454 of second arm 452 and is operably coupled with fifth swivel joint 470 so as to enable drive motor assembly 300 to rotate about fifth axis 472. In the embodiment depicted, second arm 452 can also be a telescoping arm that can selectively lengthen and retract. A motor 440F couples with second arm 452 to control the telescoping expansion and contraction of second arm 452.

As will be discussed below in greater detail, in view of the multiple swivel joints and the selective telescoping of second arm 452, adjustable arm assembly 302B can be manipulated to position impeller 64 over a wide range of positions and orientations within container assembly 16 to facilitate optimum mixing therein. Furthermore, adjustable arm assembly 302B can be programmed to periodically or continuously adjust the position of impeller 64 to optimize mixing within container assembly 16. For example, each of motors 440A-440F of adjustably arm assembly 302B and drive motor 314 of drive motor assembly 300 can be electrically connected to electrical coupler 474. In turn, electrical coupler 474 can be selectively coupled to a controller 475 having a central processing unit that can be programmed to simultaneously control operation of all the motors and thereby control not only the speed of rotation of impeller 64 but also its desired position. For example, as will be discussed below, adjustable arm assembly 302B can be used to move impeller 64 along a continuous 2-dimensional path or 3-dimensional path.

In one embodiment, each of motors 440A-F comprises an electrical motor which communicates with the corresponding swivel joints through a direct drive, gear drive, pulley system, or the like. In alternative embodiments, one or more motors can drive the swivel joints through pneumatics, hydraulics or other conventional systems. Thus, the motors need not be mounted directly to arm assembly 302B but can be located remotely with fluid lines coupled to the assembly for controlling movement.

Due to the adjustability and automated controlled movement of impeller 64 resulting from adjustable arm assembly 302B and the different configurations for container 18, mixing system 10B can operate over a higher turn-down ratio than prior embodiments. For example, mixing system 10B can be used to produce turn-down ratios in the range of at least east 50:1 or 80:1 and more commonly at least 20:1, 30:1, or 40:1. Other ratios can also be achieved.

During use of mixing systems 10A and 10B rotational assembly 48 (FIG. 2) of container assembly 16 is directly coupled within drive motor assembly 300. The flexible nature of container 18 enables adjustable arm assemblies 302A and 302B to freely tilt and to move vertically and horizontally each of drive motor assembly 300, rotational assembly 48, drive shaft 362 and impeller 64 during the rotation of impeller 64. However, in some situations container 18 may need to be oversized relative to support housing 78 when used with adjustable arm assemblies 302A and 302B so that when container 18 is filled to its maximum level with fluid, there is still a sufficient amount of flexible container 18 extending w above the fluid level to permit free movement of the assembled drive motor assembly 300, rotational assembly 48, drive shaft 362 and impeller 64.

Figure 14:
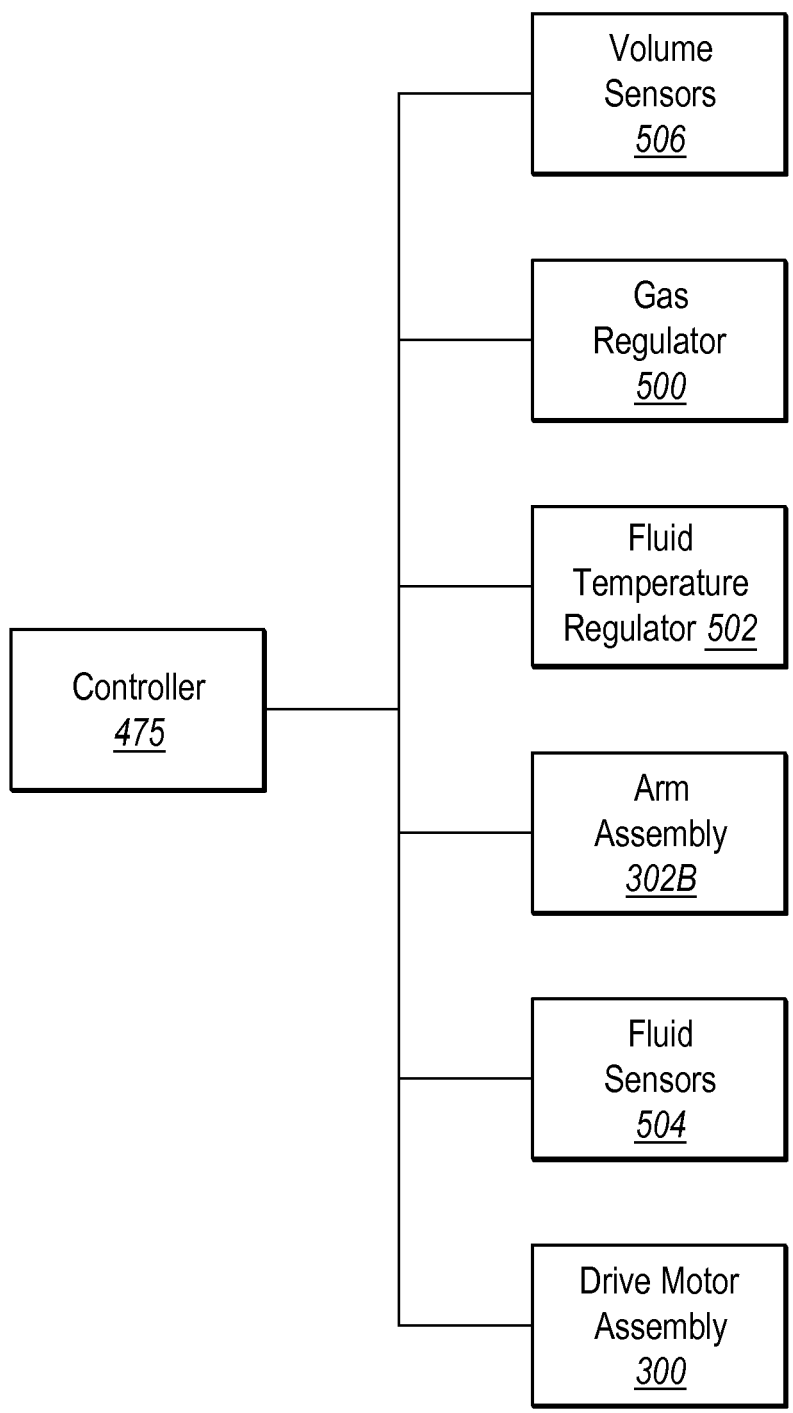
FIG. 14 is a block diagram showing the controller of the mixing system shown in FIG. 12 electrically coupled to other components of the mixing system.

Controller 475 can be electronically coupled with a variety of components of both mixing systems 10A and 10B that control operational parameters. For example, as depicted in FIG. 14, controller 475 can be electrically coupled with drive motor assembly 300, arm assembly 302B, gas regulator 500, fluid temperature regulator 502, fluid sensors 504 and volume sensors 506. Gas regulator 500 controls that flow rate and mixture of gasses that are delivered to sparger 34 through gas line 36 (FIG. 2). As previously discussed, the gases typically include air that is selectively combined with oxygen, carbon dioxide and/or nitrogen but other gases can also be used. Fluid temperature regulator 502 controls operation of the boiler that is used to heat and pump the fluid through jacketed support housing 78 for regulating the temperature of the fluid within container 18. Fluid sensors 504 are coupled with container 18 or otherwise interact with the fluid therein for detecting properties of the fluid. Examples of fluid sensors 504 include temperature probes, pH probes, dissolved $O_2$ probes, dissolved $CO_2$ probes, optical density sensors that sense the density of the fluid, conductivity sensors, and viscosity sensors.

Volume sensors 506 can come in a variety of different configurations and are used to detect the volume or level of fluid within container 18. For example, as depicted in FIG. 11, in one embodiment volume sensors 506 comprise load cells 476 positioned between support housing 78 and cart 80A. Load cells 476 provide signals to controller 475 that reflect the weight or change in weight of support housing 78 due to the addition or subtraction of fluid in container 18. In turn, controller 475 uses this information in an algorithm to calculate the volume or level of fluid within container 18. In one embodiment of the present invention means are provided for sensing the volume or level of fluid within container 18. One example of such means includes load cells 476 as discussed above. In alternative embodiments, load cells 476 can be replaced with optical sensors or pressure sensors located along the side of support housing 78 or container 18 and which sense the height of the fluid. In other embodiments floats or other mechanical sensors can be used to measure the rising or lower of the fluid within container 18. Other conventional techniques can also be used.

In one example of use, mixing systems 10A and 10B can be used as a bioreactor or fermentor for growing cells or microorganisms. A first solution having a first volume is dispensed into compartment 28 of container 18 and comprises media, cells or microorganisms, and other components as desired. The solution can be a small volume that contains an initial seed inoculum or a larger volume of a partially processed culture that is being moved to a larger container for further growth. By using a corresponding adjustable arm assembly 302A or B, impeller 64 is moved to the desired location within compartment 28 to facilitate desired mixing for the first volume of fluid. Impeller 64 is activated and set to run at a defined speed causing mixing of the solution while gas is delivered to sparger 34 to oxygenate and regulate other mass transfer with the solution. In addition, fluid temperature regulator 502 is set to heat the fluid within container 18 to a desired level. Under these conditions, the cells/microorganisms are left to propagate within the solution.

As the cell density increases, additional media can be added either at a continuous flow rate or as a batch at staggered intervals. In either event, the media is added so that the density of the cells/microorganisms does not exceed a predetermined maximum density for optimal growth and does not drop below a predetermined minimum density for optimal growth. The density values are generally more important for the growth of cells than microorganisms.

If the fluid volume increases within container 18 while impeller 64 is held at a constant speed and position, the mixing efficiency of the fluid will eventually begin to decrease. A decrease in mixing efficiency can decrease the growth rate of the cells/microorganisms and eventually result in cells/microorganisms dying due to a lack of proper mass transfer and the inability to access and consume needed nutrients from the media. According, to maintain desired mixing without transferring the solution to a new container, once the solution has reached a predetermined second volume or height within container 18, such as determined by volume sensor 506, impeller 64 is raised to a second position within container 18 which is more optimal for mixing the solution at the increased volume. This adjustment of impeller 64 can be through manual manipulation of arm assembly 302B, manually inputting commands into controller 475 for repositioning arm assembly 302B, or preprogrammed automatic adjustment of arm assembly 302B by controller 475 based on inputs from volume sensor 506.

In situations where arm assembly 302 is being adjusted manually or through manual inputs, the interval between adjustments many be longer and the moved displacement of impeller 64 greater. The addition of solution and the vertical movement of impeller is at a slower rate for small volumes of fluid and increases as the size of the culture increases. However, in some situations where the vertical movement of impeller 64 is in a single movement, the displacement of impeller may be at least 5 cm, 10 cm, 20 cm, or more. In contrast, where impeller 64 is being automatically adjusted through programmed controller 475, the movement of impeller 64 can be at much shorter intervals and at much smaller increments and in some situations, such as for large volumes of fluid, the movement of impeller 64 can be continuous.

It is envisioned that impeller 64 will be moved to the second elevated position during continuous operation of impeller 64. In some situations, however, impeller 64 can be stopped, moved to the second position, and then restarted. Once impeller 64 is moved to the second position, the process is repeated. That is, the density of the cells/microorganisms is monitored, additional media is added to the culture to regulate density, and impeller 64 is moved, either continuously or in one or more steps, to a third position to continue to maintain desired mixing conditions. In contrast to adding media based on cells/microorganism density, the media can be added at a fixed rate, at set intervals, or based on other measured processing parameters. The process of adjusting impeller 64 is continued until container 18 is either filled to a desired level and the solution is then moved to a larger container 18 for further processing or the desire batch volume is reached. Where a desired batch volume is reached, it is appreciated that impeller 64 can also be incrementally or continuously lowered within container 18 as solution is drawn out of container 18.

It is appreciated that as the volume of solution increases within container 18 and/or impeller 64 is raised, that other operating parameters also need to be continually monitored and adjusted. For example, the concentrations and rate of gas introduced through sparger 34 will likely need to be modified so that the pH and dissolved $CO_2$ and $O_2$ are within desired limits. Likewise, the temperature or flow rate of the heated fluid passing through jacketed support housing 78 may need to be adjusted to control the desired temperature of the increased volume of fluid.

In addition to or instead of adjusting the vertical height of impeller 64, the speed, tilt, and/or lateral position of impeller 64 can also be adjusted. For example, prior to or concurrent with the vertical raising or lower of impeller 64, the rotational speed of impeller 64 can be adjusted to account for the increase or decrease in fluid volume. This adjustment can be manual or automatic through controller 475 based on the sensed change in volume or fluid height. For example, when the fluid volume within container 18 gets relatively small, the speed of impeller 64 necessary to maintain proper mixing can be reduced. Failure to reduce impeller speed in low fluid volumes can result in unwanted gas entrapment and splashing of the solution. Likewise, as the fluid volume increases, it may be necessary to increase the impeller speed in addition to moving the impeller to achieve a desired mixing.

Tilting impeller 64 can adjust the circulation flow. For example, increasing lateral tilt decreases radial flow in favor of a more random flow. Tilting impeller 64 by a few degrees may thus be sufficient to maintain desired mixing at some increased fluid volumes. Periodic or continuous tilting of impeller 64 back and forth over a range of angles can also be used as one mechanism for maintaining desired mixing conditions.

Lateral displacement of impeller 64 within container 18 also influences the flow pattern of the fluid within container 18 and thus the mixing thereof. Depending on the configuration of container 18 within support housing 78, optimal fluid mixing may be achieved by locating impeller 64 at different lateral positions within container 18 as the level of the fluid within container 18 changes. In addition, periodic or continuous changing of the lateral position of impeller 64 can periodically or continuously change the flow pattern of the fluid and thus be used to achieve desired mixing conditions. For example, controller 475 can be programmed to operate arm assembly 302B so that impeller 64 is periodically or continuously moved along a fixed or random horizontal 2-dimensional path within container 18. This may be particularly helpful where the fluid volume in container 18 is so large that keeping impeller 64 at a fixed location will not be sufficient to maintain desired mixing of the entire fluid volume.

In still other embodiments, it is appreciated that controller 475 can be programmed to operate arm assembly 302B so that rotational speed, tilt, lateral displacement and/or vertical displacement of impeller 64 can be periodically or continuously adjusted to achieve desired mixing conditions as the volume of fluid increases. For example, in bioreactors and fermentors it is desirable to continually maintain a high turnover rate of the fluid within container 18 to ensure that the cells and/or microorganisms are uniformly dispersed and are exposed to a uniform feed material. One approach to increasing turnover is to just increase the impeller rotation speed. However, by just increasing impeller rotation speed, a vortex can be formed in the fluid that can decrease fluid turnover. That is, all the fluid is simply spinning within container 18 but without effectively mixing. The formation of a vortex can also entrap gas within the fluid which can be detrimental to the cells. To counter the formation of a vortex, controller 475 can be programmed to continuously or periodically adjust the position and/or orientation of impeller 64. For example, impeller 64 can be adjusted horizontally, vertically and/or tilted in different orientations. By changing the position and/or orientation of impeller 64 the force on the fluid is changed which disrupts or prevents the formation of a vortex and produces a more turbulent flow. Thus, controller 475 can be programmed to operate arm assembly 302B so that impeller 64 is periodically or continuously moved along a fixed or random 3-dimensional path within container 18. In addition to moving along the 3-dimensional path, the speed and tilt of impeller 64 can also be adjusted.

Figure 17:
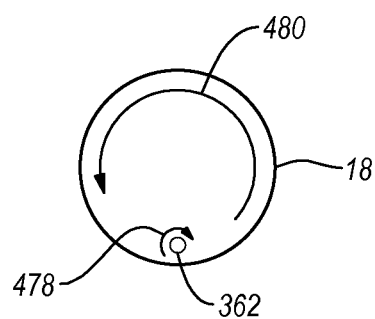
FIG. 17 is a schematic top plan view of the support housing shown in FIG. 11 showing rotation and movement of the drive shaft.

In one embodiment to help prevent the formation of vortexes, drive shaft 362 and associated impeller 64 can be moved in a pattern opposite to the direction in which impeller 64 rotates. For example, FIG. 17 shows a cross sectional top plan schematic view of container assembly 18 having drive shaft 362 disposed therein. Drive shaft 362, and thus impeller 64, can be rotated by drive motor assembly 300 in a clockwise direction as identified by arrow 478. Concurrently, however, adjustable arm assembly 302B can be moving drive shaft 362 and impeller 64 within container assembly 16 in a counterclockwise path along arrow 480. This movement in opposite directions can help eliminate the formation of a vortex.

This automatic adjusting of the impeller location and speed can have a significant influence during critical applications. For example, in the final fill volume of bioreactors, aluminum or other solutes, adjuvants and/or suspensions are commonly added to boost or stabilize the dose potency. In this case the dense materials can settle out very easily and the solution must remain well mixed until the final few liters are drained. By automatically adjusting the impeller location as the fluid level lowers there is a decreased chance of any unwanted settling.

In some embodiments, such as when cells are being grown on micro carriers in a bioreactor, it can be desirable to minimize impeller speed since contact between the cells and a fast rotating impeller can damage the cells. As mentioned above, the speed of the impeller is often dictated by the need for maintaining a continuous turnover of the fluid. To help minimize damage by impeller 64 while maintaining desired fluid mixing, adjustable arm assembly 302B can continuously or periodically move impeller 64 in a horizontal pattern within container 18, such as along the circular path of arrow 480 in FIG. 16. This horizontal movement of impeller 64 enables impeller 64 to have lower tip speed or rotational speed which minimizes cell damage but still maintain a generally uniform mixing of the fluid. It is appreciated that impeller 64 can be moved in a variety of different patterns such as a triangle or other polygonal patterns or in a repeating wave pattern. Varying the tilt of impeller 64, either in conjunction with or independent of the horizontal movement of impeller 64, can also help achieve uniform mixing at low impeller speed.

In other embodiments, it appreciated that controller 475 can be operated by a automated program that uses computational fluid dynamic modeling in conjunction with sensed critical process variables to provide real time feedback for dynamically controlling the position, speed, orientation, and/or movement pattern of impeller 64. For example, based on input from fluid sensors 504 and volume sensors 506, controller 475 can monitor the process variables of volume, gassing rate, pH, dissolved $O_2$, dissolved $CO_2$, conductivity, density, viscosity, and/or flow pattern of the solution. When any of the process variables fall outside of a predefined range, controller 475 automatically makes adjustments to gas regulator 500, fluid temperature regulator 502, arm assembly 302B and/or drive motor assembly 300 to correct the process variable. The algorithm used to correct the process variable is based on known computational fluid dynamic modeling techniques and empirical data. Where applicable, controller 475 can dynamically regulate the position, speed, orientation, and/or movement pattern of impeller 64 through arm assembly 302B and drive motor assembly 300 to correct the processing variable. For example, if the cell or microorganism density is found to be too high at a certain location within container 18, as could be determined by multiple optical density sensors couple about container 18, impeller 64 may be automatically moved to a defined location within container 18 to improve the overall mixing of the fluid or may be temporarily moved closer to the location where the cells/microorganism have the highest density so that those cells/microorganism are properly mixed. Alternatively, as controller 475 senses that the volume of fluid within container has reached a predefined level, controller 475 can automatically set impeller 64 to move to certain locations or to travel along a certain 2- or 3-dimensional path. It is appreciated that the possible alternatives as to when and how the position, speed, orientation, and/or movement pattern of impeller 64 can be adjusted are extensive. The programmed system, however, continuous to make dynamic adjustments to the system based on real time sensed processing parameters until processing of the fluid is completed.

Figure 15:
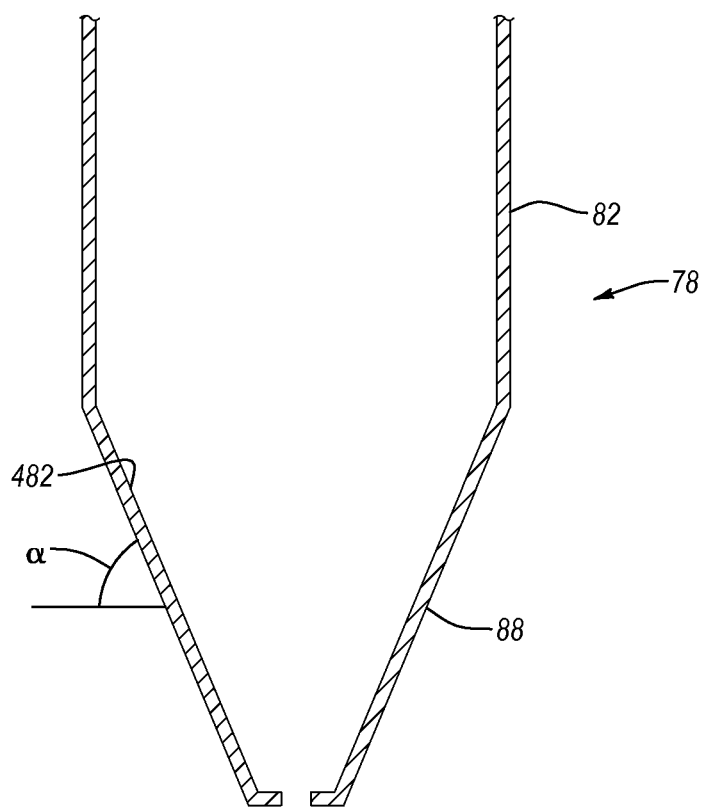
FIG. 15 is a cross sectional side view of one embodiment of the support housing shown in FIG. 11.

To enable mixing of solutions at very low volumes, it is appreciated that floor 88 or the lower end of support housing 78 can be made having a steep conical configuration into which container 18 having a complementary configuration can be received and impeller 64 can be lowered. For example, depicted in FIG. 15 is a cross sectional side view of one embodiment of support housing 78 in which floor 88 has a conical configuration with an interior surface 482 sloping at an angle α relative to the horizontal. The angel α can be in a range between about 35° to about 70° with about 45° to about 70° and about 55° to about 70° being more common. Other angles can also be used. By inwardly tapering the floor or lower end of support housing 78, smaller volumes of solution can be formed within container 18 that retain a sufficient depth and width to enable impeller 64 to be lowered therein. Impeller 64 can thus be submerged and rotated within the smaller volumes to maintain proper mixing.

Figure 16:
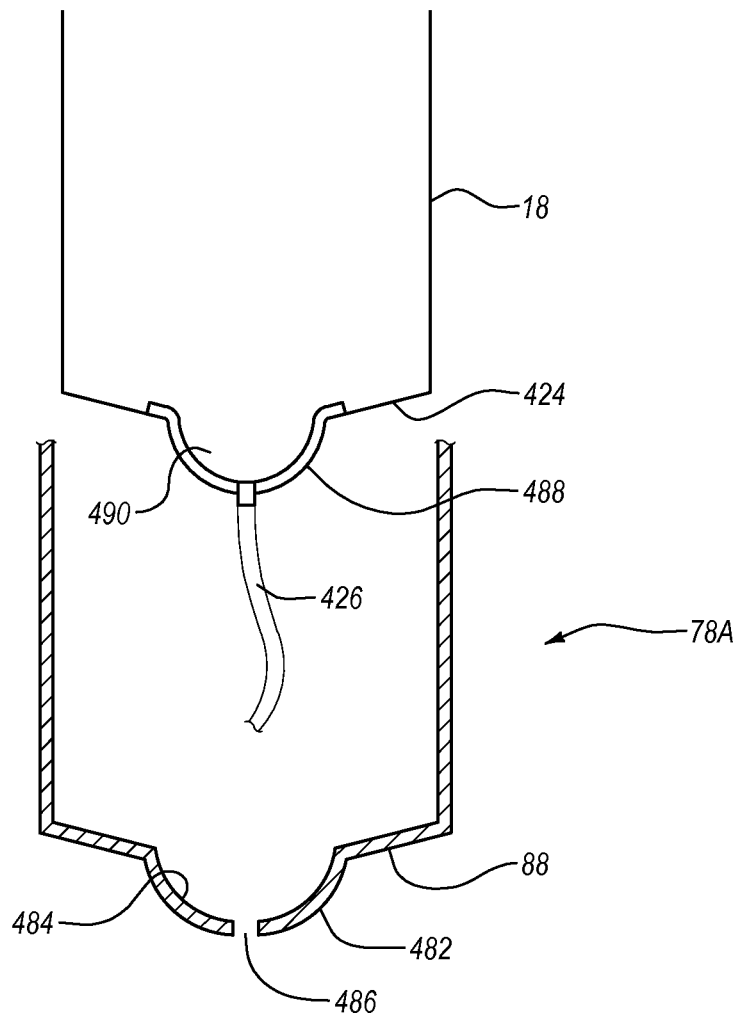
FIG. 16 is a cross sectional side view of an alternative embodiment a flexible container having a dish mounted to the floor thereof and a support housing configured to receive the container.

Depicted in FIG. 16 is another alternative embodiment of how a container and corresponding support housing can be formed to permit proper mixing at both large and small volumes of solution. As shown therein, a support housing 78A is formed having a sidewall that extends down to floor 88. Centrally formed on floor 88 is a receiver 482 that bounds a recess 484. In the depicted embodiment, receiver 482 and recess 484 have a semi-spherical configuration. In other embodiments, receiver 482 and recess 484 can have other shapes. Floor 88 is annular and slopes toward receiver 482. A port 486 is centrally formed through the bottom of receiver 482.

Container 18 is shown having floor 424. Centrally secured to floor 424, such as by welding, is a dish 488 which bounds a cavity 490. Fluid line 426 couples with the bottom of dish 488 so as to communicate with cavity 490. During assembly, dish 488 is received and supported within receiver 482 so that fluid line 426 passes out through port 486. Receiver 482 typically has a configuration complementary to dish 488. Dish 488 can be comprised of a rigid or semi-rigid material such as a plastic or composite. Alternatively, dish 488 can be formed from a polymeric sheet or film, such as that used to form container 18.

As the solution is drained out of container 18 or as the solution is initially dispensed into container 18, the solution gathers within dish 488. Again, dish 488 has a width and depth that enables impeller 64 to be lowered therein. Impeller 64 can thus be submerged and rotated within cavity 490 to maintain proper mixing of the relatively small volume of fluid container therein. Dish 488 is typically configured so that cavity 490 has a semi-spherical configuration or an elongated semi-spherical configuration. However, cavity 490 can also be formed into other configurations that will receive impeller 64. Cavity 490 can have a volume in a range between about 5 liters to about 40 liters with about 5 liters to about 20 liters or 5 liter to about 10 liters being more common.

As with other embodiments, it is appreciated that adjustable arm assembly 302B can be used in association with container 404, depicted in FIG. 9, which is an open top liner. Again, rotational assembly 48 can be used to secure impeller assembly 40 to drive motor assembly 300 or, as shown in FIG. 10, rotational assembly 48 can be replaced by a clamp 406 that secures tubular connector 44 to drive shaft 362.

Figure 18:
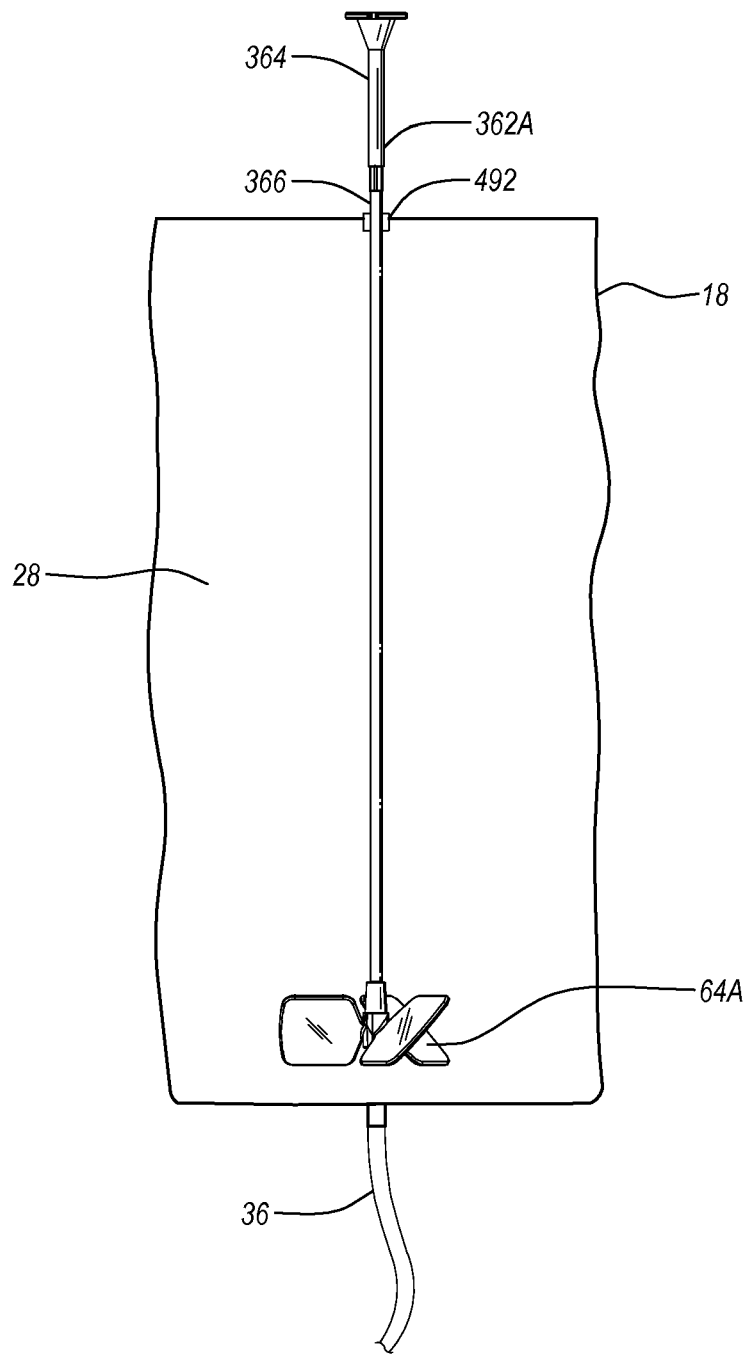
FIG. 18 is a cross sectional side view of an alternative embodiment of a drive coupled to a flexible container by a dynamic seal.

In another alternative embodiment, it is appreciated that impeller assembly 40 (FIG. 3) can be eliminated. For example, as shown in FIG. 18, container 18 has a drive shaft 362A that projects directly into compartment 28. Drive shaft 362A can have substantially the same configuration as drive shaft 362 except that an impeller 64A is rigidly fixed directly to the end thereof within compartment 28. A dynamic seal 492 is used to form an aseptic seal between container 18 and shaft section 366 of drive shaft 362A. Seal 492 also enables drive shaft 362A to rotate relative to container 18 while maintaining the aseptic seal.

Drive shaft 362A includes head section 364 which threads or otherwise secures to shaft section 366 as shown in FIG. 3. Head section 364 can thus be attached to drive motor assembly 300 (FIG. 11) prior to securing head section 364 to shaft section 366. Alternatively, drive shaft 362A can be formed as a single integral member and a different structure can be used to secure drive shaft 362A to drive motor assembly 300. Shaft section 366 or the entire drive shaft 362A can be made from a plastic or composite material that is disposed of after use. Alternatively, shaft section 366 or the entire drive shaft 362A can be made of a metal that is sterilized and reused.

Adjustable arm assembly 302B is only one example of a programmable robotic arm that can be used with the present invention. It is appreciated any number of conventional robotic arms can be used in the present invention. Furthermore, it is appreciated that other robotic arms need not have all of the degrees of freedom incorporated into adjustable arm assembly 302B. For example, the robotic arm may only be able to move impeller 64 vertically up and down but not move laterally or tilt. Other robotic arms may have any combination of being able to move impeller 64 vertically, laterally, and/or tilt. Thus, the robotic arms can be designed to move impeller 64 in one dimension, two dimensions, or three dimensions. It is likewise appreciate that adjustable arm assembly 302B need not be in the shape of a conventional robotic arm. For example, adjustable arm assemblies 302A can be modified to incorporate motors for moving the various supports and those motors can be electronically coupled to controller 475 for automatically controlling the movement of impeller 64.

The above discussed embodiments disclose impeller 64 as the sole mixing element. In other embodiments, however, it is appreciated that impeller 64 can be replaced with other mixing elements. For example, a magnetically driven impeller could be rotatably mounted on the end of dive shaft 362. Although drive shaft 362 could still be used to elevate, tilt, or move the impeller in a pattern, a magnetic drive source located outside of container 19 could be used to rotate the impeller. As such, drive motor assembly 300 could be eliminated. In another embodiment, the ends of a fluid inlet tube and a fluid outlet tube could be mounted on the end of draft shaft 362. Fluid could be drawn out of container 18 through the outlet tube while the fluid is pumped back into container 18 through the inlet tube. The fluid being drawn out of and pumped into container 18 can mix the remaining fluid within container 18. Again, drive shaft 362 can be used to elevate, tilt, or move the ends of the tubes. In another embodiment, the end of a gas line can be mounted to the end of drive shaft 362. The gas blown out of the gas line can be used to mix the fluid. In still other embodiments, impeller 64 can be replaced with a paddle, baffle, or other structure that can be swiveled, rotated, reciprocated, pivoted or otherwise moved within container 18 for mixing the fluid therein.

The inventive fluid mixing systems achieve a number of benefits. By way of example, the inventive systems permit fluids, and particularly cell and microorganism cultures, to be processed within a single container over a significantly larger turn down ratio than prior systems. Notably, the fluid mixing systems enable fluids to be mixed within a single container at a desired turnover or mixing rate over a broad range of fluid volumes. As a result of eliminating or reducing the number of different containers that the fluid has to be transferred into during processing, there is less downtime where the fluid is not being mixed or otherwise treated, less material waste, lower labor costs, and less risk of fluid contamination. Furthermore, the inventive mixing systems provide improved mixing capabilities and improved fluid processing capabilities.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of mixing a fluid for a bioproduction process, comprising:
   providing a container and a drive shaft having a first end and a second end, a mixing element being operably coupled to the first end of the drive shaft, the mixing element being disposed within an interior of the container;
   operably connecting the second end of the drive shaft to a drive motor assembly;
   adjusting a vertical height of the mixing element relative to the container;
   moving the mixing element through use of the drive motor assembly to mix a fluid within the container; and
   controlling a vertical height, a vertical displacement, and a speed of the mixing element during the mixing by adjusting a position of an arm, wherein the arm is operably coupled to the drive shaft.

2. The method of claim 1, further comprising the steps of:
   changing a volume of the fluid within the container while mixing; and
   adjusting the height of the mixing element based on the volume of the fluid.

3. The method of claim 2, further comprising the step of maintaining an optimal location of the mixing element based on the volume of the fluid.

4. The method of claim 3, wherein the optimal location is determined based on the volume of fluid within the interior of the container and the volume of fluid is predetermined using a cell density range.

5. The method of claim 2, further comprising the step of continuously adjusting the vertical displacement of the mixing element during the mixing.

6. The method of claim 2, further comprising the step of periodically adjusting the vertical displacement of the mixing element during the mixing.

7. The method of claim 1, further comprising the step of sensing a volume of the fluid using a sensor.

8. The method of claim 7, further comprising the step of providing a controller that is electronically coupled to the sensor and the arm is adjusted based on a measurement of the sensor.

9. The method of claim 8, wherein the sensor is a load cell.

10. The method of claim 8, wherein the sensor is an optical sensor.

11. The method of claim 8, wherein the sensor includes a float.

12. The method of claim 1, further comprising the step of supporting the container with a support housing.

* * * * *